US012404543B2

(12) United States Patent
Mollerup

(10) Patent No.: US 12,404,543 B2
(45) Date of Patent: Sep. 2, 2025

(54) HYBRIDIZATION COMPOSITIONS AND METHODS FOR MAKING AND USING COMPOSITIONS

(71) Applicant: Agilent Technologies, Inc., Santa Clara, CA (US)

(72) Inventor: Jens Mollerup, Roskilde (DK)

(73) Assignee: Agilent Technologies, Inc., Santa Clara, CA (US)

( * ) Notice: Subject to any disclaimer, the term of this patent is extended or adjusted under 35 U.S.C. 154(b) by 794 days.

(21) Appl. No.: 16/854,618

(22) Filed: Apr. 21, 2020

(65) Prior Publication Data
US 2020/0340047 A1    Oct. 29, 2020

Related U.S. Application Data

(60) Provisional application No. 62/848,964, filed on May 16, 2019, provisional application No. 62/838,813, filed on Apr. 25, 2019.

(51) Int. Cl.
*C12N 15/10* (2006.01)
*C12Q 1/6832* (2018.01)
*C12Q 1/6841* (2018.01)

(52) U.S. Cl.
CPC ......... *C12Q 1/6841* (2013.01); *C12Q 1/6832* (2013.01)

(58) Field of Classification Search
CPC ................ C12N 15/1003; C12Q 1/6813
See application file for complete search history.

(56) References Cited

U.S. PATENT DOCUMENTS

| | | | |
|---|---|---|---|
| 5,853,986 A | 12/1998 | Petrie, III et al. | |
| 5,958,689 A * | 9/1999 | Scholin ............... | C12Q 1/6895 435/6.12 |
| 6,730,474 B1 | 5/2004 | van Dongen et al. | |
| 7,105,294 B2 | 9/2006 | Van Dongen et al. | |
| 2003/0113605 A1* | 6/2003 | Hidaka et al. ...... | H01M 8/1025 429/492 |
| 2005/0266459 A1 | 12/2005 | Poulsen et al. | |
| 2010/0075335 A1* | 3/2010 | Ramos Franco Tavares ............... | C12Q 1/6816 435/6.11 |
| 2011/0229975 A1* | 9/2011 | Matthiesen ......... | C12Q 1/6832 536/25.3 |
| 2011/0236997 A1* | 9/2011 | Battersby ............ | C12Q 1/6834 436/501 |
| 2014/0120535 A1 | 5/2014 | Aurich-Costa et al. | |
| 2014/0256585 A1 | 9/2014 | McCoy | |
| 2019/0054175 A1 | 2/2019 | Soane et al. | |

FOREIGN PATENT DOCUMENTS

| | | | | |
|---|---|---|---|---|
| CN | 103966321 A | 8/2014 | | |
| CN | 104032033 A | 9/2014 | | |
| JP | 2012518430 A | 8/2012 | | |
| WO | 9914226 | 3/1999 | | |
| WO | 2003027328 | 4/2003 | | |
| WO | 2009144581 | 12/2009 | | |
| WO | 2010080566 A1 | 7/2010 | | |
| WO | 2010097707 | 9/2010 | | |
| WO | 2011067678 A2 | 6/2011 | | |
| WO | 2011067678 A3 | 8/2011 | | |
| WO | 2014131906 A1 | 9/2014 | | |
| WO | 2014176575 A1 | 10/2014 | | |
| WO | 2015103287 A2 | 7/2015 | | |
| WO | 2015184144 A1 | 12/2015 | | |
| WO | WO-2015200139 A1 * | 12/2015 | ........... | C12Q 1/6804 |
| WO | 2016125091 A1 | 8/2016 | | |
| WO | WO-2017147483 A1 * | 8/2017 | ............. | C12Q 1/682 |

OTHER PUBLICATIONS

Genet, et al., "Direct DNA and PNA Probe Binding to Telomeric Regions Without Classical In Situ Hybridization", Molecular Cytogenetics, vol. 6, No. 42, 2013, 1-5.
Kuwajima, et al., "Cleart : A Detergent—And Solvent-Free Clearing Method for Neuronal and Non-Neuronal Tissue", Development, vol. 140, 2013, 1364-1368.
Laneve, et al., "The Gcm/Glide Molecular and Cellular Pathway: New Actors and New Lineages", Developmental Biology, vol. 375, 2013, 65-78.
Massey, et al., "A Fluorescent Molecular Switch for Room Temperature Operation Based on Oligonucleotide Hybridization Without Labeling of Probes or Targets", Analytica Chimica Acta, vol. 750, 2012, 182-190.
Poulsen, et al., "Comparison of Fluorescence In Situ Hybridization and Chromogenic In Situ Hybridization for Low and High Throughput HER2 Genetic Testing", International Journal of Breast Cancer, vol. 2013, Article ID 368731, 2013, 1-5.
Tafe, et al., "Rapid Fluorescence In Situ Hybridisation (FISH) for HER2 (ERBB2) Assessment In Breast and Gastro-Oesophageal Cancer", Journal of Clinical Pathology, vol. 68, Jan. 9, 2015, 306-308.
Kurreck, J., "Antisense technologies: Improvement through novel chemical modifications," Eur. J. Biochem., 2003, vol. 270, pp. 1628-1644.
Powell, R.D. et al., "Metallographic in situ hybridization," Hum. Pathol., 2007, vol. 38(8), pp. 1145-1159
Arora, et al., "Immobilization of Single Stranded Dna Probe Onto Polypyrrole-Polyvinyl Sulfonate for Application to Dna Hybridization Biosensor", Sensors and Actuators B: Chemical, vol. 126, 2007, 655-663.
Notification of Transmittal of The International Search Report and Written Opinion mailed on Jul. 27, 2020, Application No. PCT/US2020/029123, 14 pages.
EPO, "Extended European Search Report mailed on Jan. 4, 2023," Application No. 20795136.9, 8 pages.

* cited by examiner

Primary Examiner — Bradley L. Sisson

(57) ABSTRACT

The present disclosure relates to hybridization buffers for use in hybridization, for example, for use in in situ hybridization (ISH). Hybridization buffers and compositions comprising a sulfone solvent and polyvinyl sulfonic acid or a salt thereof, and methods of making and using, the same are disclosed.

17 Claims, 4 Drawing Sheets

HYBRIDIZATION COMPOSITIONS AND METHODS FOR MAKING AND USING COMPOSITIONS

CROSS-REFERENCE TO RELATED APPLICATIONS

This application claims benefit of the filing dates and rights of priority to U.S. Provisional Application No. 62/838,813, filed Apr. 25, 2019, and U.S. Provisional Application No. 62/848,964, filed May 16, 2019, both of which are incorporated by reference herein.

FIELD OF THE INVENTION

The present disclosure relates to hybridization buffers for use in hybridization methods, for example, for use in in situ hybridization (ISH) methods. More generally, the present disclosure relates to the fields of cytology, histology, and molecular biology.

BACKGROUND OF THE INVENTION

Hybridization is an important and well-known property of nucleic acids. The double helix structure of DNA is stabilized by hydrogen bonding between bases on opposite strands when bases are paired in one particular way (A+T or G+C). In a basic example of hybridization, nucleic acid fragments or sequences bind to a complementary nucleic acid fragment or sequence. Hybridization assays and other methods use nucleic acid probes designed to specifically bind with a target nucleic acid, for example, DNA or RNA. One type of hybridization assay, in situ hybridization (ISH), includes hybridization of a nucleic acid probe to a target nucleic acid in a specimen wherein the sample may be in vivo, or for example, fixed or adhered to a glass slide. The probes may be labeled to make it possible to identify a probe-target hybrid by use of a fluorescence or bright field microscope/scanner. For nucleic acid targets, the probe is typically a double or single stranded nucleic acid, such as a DNA, RNA, or analogs. In some embodiments, the probe may be labeled using radioactive labels such as $^{31}P$, $^{33}P$, $^{32}S$, non-radioactive labels such as digoxigenin and biotin, or fluorescent labels. Such labeled probes can be used to detect genetic abnormalities in a target sequence, providing valuable information about, e.g., prenatal disorders, cancer, and other genetic or infectious diseases.

The efficiency and accuracy of nucleic acid hybridization assays mostly depend on at least one of three major factors: a) denaturation (i.e., separation of, e.g., two nucleic acid strands) conditions, b) renaturation (i.e., re-annealing of, e.g., two nucleic acid strands) conditions, and c) post-hybridization washing conditions.

Traditional hybridization methods, such as ISH assays, have used formamide-containing solutions to denature doubled stranded nucleic acid targets. Formamide is very effective as a denaturing solvent, but formamide is atoxic hazardous material, subject to strict regulations for use and waste. Moreover, the use of formamide increases the time required to complete the hybridization assay, depending on the conditions and the nucleic acid fragments or sequences used. For example, the denaturation step is followed by a longer time-consuming hybridization step, which, e.g., in a traditional fluorescent in situ hybridization (FISH) protocol takes 14-24 hours, and can even take up to 72 hours.

The step of re-annealing (i.e., hybridizing) two complementary strands of nucleic acid chains is a time-consuming aspect of an assay using hybridization. Chaotropic agents, such as formamide, guanidinium hydrogen, and urea, which interfere with the Watson-Crick binding sites of nucleic acid bases and thereby disturb the hydrogen bonds between complementary nucleic acid bases, have been used to lower the melting temperature (Tm) of the complementary chains. However, although the use of chaotropic agents lowers the Tm, these agents prolong the hybridization time compared to hybridization in an aqueous solution without a chaotropic agent.

Certain existing hybridization buffers exhibit wide variation with respect to the amount of time required to perform in situ hybridizations on formalin fixed and paraffin-embedded (FFPE) tissue. For example, some prior hybridization buffers require over-night incubations while certain improved compositions only require incubations of 1 to 2 hours (see, e.g., US 20110229975 and US 20110236997, hereby incorporated by reference in their entireties). Shorter incubation durations are preferred and hybridization buffers providing such advantages are desirable. IQFISH Fast Hybridization Buffer was introduced by Agilent Technologies, Inc. as a significant improvement over prior teratogenic formamide compositions, representing a safety advantage for personnel working with in situ hybridization techniques. The improved buffer also significantly reduced the time required for hybridizations to 1 to 2 hours.

However, while the faster incubation times of certain existing hybridization buffers are highly desirable and a significant improvement, there are certain characteristics of hybridization buffers that could be further improved to provide a hybridization buffer that is more stable and easy to use. Accordingly, there remains a need in the art for hybridization buffers that maintain the short 1 to 2 hour incubations while exhibiting one or more additional improvements such as lower viscosity, higher stability, higher homogeneity, and more flexible storage and mixing requirements.

Certain existing hybridization buffers exhibit slow, non-robust spreading in capillary fields formed between glass slides, for example. This is undesirable as it may leave airspaces where functionality of the hybridization buffer is absent.

Certain existing ISH hybridization buffers generally must be stored at temperatures of −18° C. or lower. At such storage temperatures, such buffers tend to solidify, form extensive precipitates and/or exhibit phase separation. Therefore, prior to use, many hybridization buffers must be thawed and equilibrated to 20-25° C., then extensively mixed to solubilize precipitates and homogenize liquid phases. Immediately after use, these hybridization buffers must be refrozen at temperatures below −18° C. Therefore, such hybridization buffers are susceptible to freeze thaw damage and may only withstand about 10 cycles of freezing and thawing.

Certain existing hybridization buffers also exhibit inhomogeneity at low temperatures and in some instances, special attention to temperature equilibration and the mixing process is required. In some cases, a separate instrument, such as a Dako Omnis Mixing Device, need to be used for thawing and homogenization of probe products in certain existing hybridization buffers prior to use.

In addition, certain existing hybridization buffers exhibit instability. For example, buffers that utilize ethylene carbonate as the solvent may exhibit instability due to hydrolysis of ethylene carbonate. Ethylene carbonate hydrolysis is temperature dependent, and, accordingly, buffers that include ethylene carbonate are less desirable for use at temperatures above 66° C.

Matthiesen et al. WO 2009/144581, the disclosure of which is incorporated herein by reference in its entirety, provides methods and compositions for hybridizing at least one molecule to a target. The methods and compositions may, for example, eliminate the use of, or reduce the dependence on formamide in hybridization. These compositions comprise an aqueous composition comprising at least one polar aprotic solvent in an amount effective to denature double-stranded nucleotide sequences.

Matthiesen WO2010/097707, the disclosure of which is incorporated herein by reference in its entirelty, provides methods and compositions for separately denaturing a probe and target in hybridization applications. The methods and compositions may, for example, eliminate the use of, or reduce the dependence on formamide in hybridization applications. These compositions comprise an aqueous composition comprising at least one polar aprotic solvent in an amount effective to denature double-stranded nucleotide sequences.

Battersby et al. US Patent App. Pub. No. 20110236997 describes methods and reagents for hybridization assays. Specific sulfonic acid polymers and hybridization conditions are said to lead to shorter incubation times.

SUMMARY OF THE INVENTION

As one aspect, the present disclosure provides hybridization buffers comprising: a sulfone solvent in a concentration from about 5 to about 30% (v/v); and a sulfonic acid polymer of formula (I), (Ia), (II), (IIa) or (III):

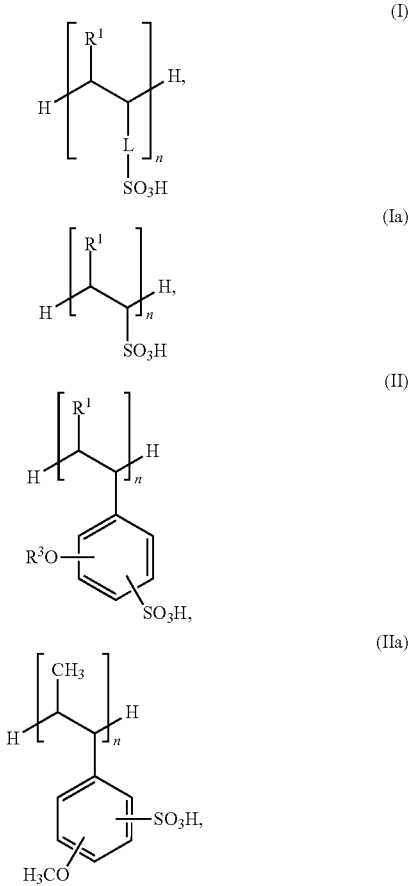

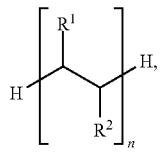

or a salt of any one of Formulas (I), (Ia), (II), (IIa) or (III), wherein: $R^1$ is hydrogen or $C_{1-6}$ aliphatic; L, when present, is a covalent bond or $C_{1-6}$ aliphatic, $R^2$, when present, is a covalent bond, $C_{1-6}$ aliphatic, phenyl, or a 6-membered heteroaryl ring having 1-3 nitrogens, wherein: $R^2$ is substituted with 1 or 2-$SO_3H$ groups or a salt thereof, provided that when $R^2$ is a covalent bond, only 1-$SO_3H$ group or a salt thereof is present, and $R^2$ is optionally substituted with 1-2 groups independently selected from —$R^3$, halogen, —CN, —$NO_2$, —$OR^3$, —$N(R^3)_2$, and —$SR^3$, wherein each $R^3$ is independently hydrogen or a $C_{1-6}$ alkyl group; and n is an integer greater than 10; and wherein the sulfonic acid polymer or salt thereof is present in a concentration from about 5 to about 50% (w/v). In some embodiments, $R^1$ is hydrogen. In other embodiments, $R^1$ is $C_{1-6}$ aliphatic. In certain embodiments, L is a covalent bond. In other embodiments, L is $C_{1-6}$ aliphatic. In additional embodiments, L is methylene.

In some embodiments, the hybridization buffers of the present technology further comprise water. In some embodiments, the sulfonic acid polymer or salt thereof is polyvinylsulfonic acid or a salt thereof. In other embodiments, the concentration of the sulfone solvent is from about 10% to about 20% (v/v). In additional embodiments, the sulfone solvent is selected from the group consisting of dimethyl sulfone, diphenyl sulfone, methyl phenyl sulfone, tetramethylene sulfone (sulfolane), and mixtures thereof. In other embodiments, the sulfone solvent is sulfolane.

In some embodiments, hybridization buffers of the present technology comprise the sulfonic acid polymer or salt thereof at a concentration of from about 20% to about 40% (w/v). In other embodiments, the hybridization buffers of the present technology further comprise dextran sulfate in concentration no greater than 20% (w/v), alternatively no greater than 15% (w/v), alternatively no greater than 10% (w/v).

In additional embodiments, the hybridization buffer has a viscosity at 25° C. of about 60 mPa·s or less, alternatively about 50 mPa·s or less, alternatively about 40 mPa·s or less, as measured by microviscometry. In certain embodiments, the hybridization buffers of the present technology are stable at 2-8° C. for at least 2 months, alternatively for at least 4, 6, 8, 12, 16, 18 or 24 months. In other embodiments, the hybridization buffers are homogeneous after storage at 2-8° C. for at least 2 months, alternatively for at least 4, 6, 8, 12, 16, 18 or 24 months. In some embodiments, the hybridization buffers maintain homogeneity after storage at 2-8° C. for at least 2 months, alternatively for at least 4, 6, 8, 12, 16, 18 or 24 months, wherein the homogeneity is determined by visually assessing the clarity of the hybridization buffer following centrifugation of the hybridization buffer with erioglaucine.

In some embodiments, the hybridization buffers of the present technology further comprise at least one additional component selected from the group consisting of buffering agents, salts, accelerating agents, chelating agents, detergents, blocking agents, and combinations thereof. In certain embodiments, the hybridization buffers further comprise NaCl and 3-(N-morpholino)propanesulfonic acid (MOPS).

In other embodiments, the hybridization buffers further comprise an accelerating agent in a concentration no greater than about 20% (w/v), alternatively no greater than about 10% (w/v), a salt, and a buffering agent; wherein the sulfone solvent is sulfolane in a concentration of about 10% (v/v), the sulfonic acid polymer or salt thereof is in a concentration of about 30% (w/v). In some embodiments, the hybridization buffers of the present technology further comprise at least one nucleic acid probe.

In another aspect, the present disclosure provides a method of hybridizing nucleic acid sequences comprising: applying at least one nucleic acid probe and a hybridization buffer to the target nucleic acid sequence for at least a time period sufficient to hybridize the at least one nucleic acid probe to the target nucleic acid sequence, wherein the hybridization buffer comprises a sulfone solvent in a concentration from about 5 to about 30% (v/v) and a sulfonic acid polymer of formula (I), (Ia), (II), (IIa) or (III):

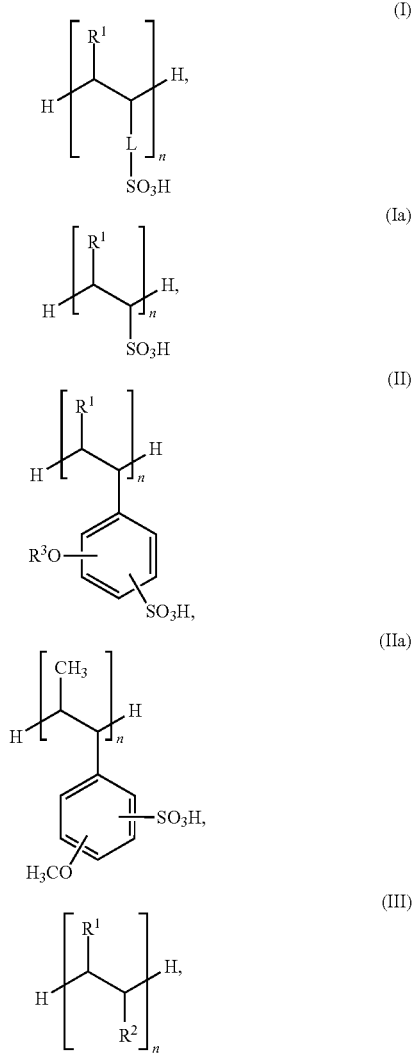

or a salt of any one of Formulas (I), (Ia), (II), (IIa) or (III), wherein: $R^1$ is hydrogen or $C_{1-6}$ aliphatic; L, when present, is a covalent bond or $C_{1-6}$ aliphatic, $R^2$, when present, is a covalent bond, $C_{1-6}$ aliphatic, phenyl, or a 6-membered heteroaryl ring having 1-3 nitrogens, wherein: $R^2$ is substituted with 1 or 2-$SO_3H$ groups or a salt thereof, provided that when $R^2$ is a covalent bond, only 1-$SO_3H$ group or a salt thereof is present, and $R^2$ is optionally substituted with 1-2 groups independently selected from —$R^3$, halogen, —CN, —$NO_2$, —$OR^3$, —$N(R^3)_2$, and —$SR^3$, wherein each $R^3$ is independently hydrogen or a $C_{1-6}$ alkyl group; and n is an integer greater than 10; and wherein the sulfonic acid polymer or salt thereof is present in a concentration from about 5 to about 50% (w/v).

In some embodiments of the present technology, the target nucleic acid sequence is present in an in situ biological sample. In other embodiments, the methods of the current technology comprise denaturing the target nucleic acid sequence at a temperature of about 65° C. or higher. In other embodiments, the methods of the current technology comprise denaturing the target nucleic acid sequence at a temperature of about 80° C. or higher. In other embodiments, the methods of the current technology comprise denaturing the target nucleic acid sequence at a temperature of about 60° C. to about 95° C., such as about 60° C. to about 70° C., or about 70° C. to about 80° C., or about 80° C. to about 90° C., or about 90° C. to about 95° C. or any temperature between any of these endpoints. In other embodiments, the present hybridization buffers will produce strong signals when the denaturation temperature is about 72° C., about 82° C., or about 92° C. In certain embodiments, the time period sufficient to hybridize the at least one nucleic acid probe to the target nucleic acid sequence is four hours or less. In other embodiments, hybridization of the at least one nucleic acid probe to the target nucleic acid is conducted at a temperature of 50° C. or lower.

In some embodiments, the methods of the current technology further comprise obtaining the hybridization buffer from storage at a temperature of 8° C. or lower and combining the hybridization buffer with the at least one nucleic acid probe without mixing the hybridization buffer prior to combining the probe therewith.

In other embodiments, the method includes the use of a sulfone solvent selected from the group consisting of dimethyl sulfone, diphenyl sulfone, methyl phenyl sulfone, tetramethylene sulfone (sulfolane), and mixtures thereof. In some embodiments, the sulfone solvent is sulfolane.

In additional aspects, the current technology provides a method of preparing a hybridization composition comprising storing a hybridization buffer at a temperature for at least 2 months, alternatively for at least 4, 6, 8, 12, 16, 18 or 24 months; and subsequently combining the hybridization buffer with at least one nucleic acid probe to form a hybridization composition. In some embodiments, the hybridization buffer is stored at a temperature greater than 0° C.

In some embodiments, the salt of polyvinyl sulfonic acid may be a sodium salt, a potassium salt, a lithium salt or any other salt suitable for the intended purpose. However, it will be appreciated that any salt of polyvinyl sulfonic acid suitable for use in a hybridization buffer may be used. In some embodiments, the hybridization buffers further comprise dextran sulfate or another accelerating agent, but in a concentration no greater than 20% (w/v), alternatively no greater than 15% (w/v), alternatively no greater than 10% (w/v), and the present disclosure provides hybridization buffers having viscosities at 25° C. of 60 mPa·s or less, alternatively 50 mPa·s or less, alternatively 40 mPa·s or less, as measured by a Lovis 2000 M microviscometer. Stability testing, including accelerated stability tests, have demonstrated that hybridization buffers of the present disclosure are stable and/or homogeneous after storage at 2-8° C. for at least 2 months, alternatively for at least 4, 6, 8, 12, 16, 18 or 24 months.

As another aspect, the present disclosure provides methods of hybridizing nucleic acid sequences. The methods comprise providing a target nucleic acid sequence, and applying a hybridization composition as disclosed herein to the target nucleic acid sequence for at least a time period sufficient to hybridize the at least one nucleic acid probe of the hybridization composition to the target nucleic acid sequence. The target nucleic acid sequence can be present in an in situ biological sample, and the methods can further comprise denaturing the target nucleic acid sequence at a temperature of about 66° C. to about 80° C. or higher and/or a hybridization step wherein the at least one nucleic acid probe and the target nucleic acid sequence are at a temperature of about 55° C. to about 50° C. or lower for 4 hours or less. In some embodiments, the methods further comprise obtaining the hybridization buffer from storage at a temperature of 2-8° C., and combining the hybridization buffer with the at least one nucleic acid probe without prior mixing of the hybridization buffer to form a hybridization composition. Once the probe and hybridization buffer are combined to produce the hybridization composition, the hybridization composition is mixed prior to use in a hybridization method, such as FISH.

As another aspect, the present disclosure provides methods of preparing a hybridization composition. The methods comprise combining a hybridization buffer with at least one nucleic acid probe to form a hybridization composition, and storing the hybridization composition at a temperature for at least 2 months, alternatively for at least 4, 6, 8, 12, 16, 18 or 24 months, such as a temperature greater than 0° C. While some embodiments of the present hybridization buffers are homogeneous and do not require mixing prior to use, probe containing hybridization compositions should, in certain embodiments, be mixed prior to use in hybridization methods.

The present disclosure provides hybridization buffers and methods that are, for example, homogeneous and stable across a wide variety of storage conditions. For instance, certain embodiments of the present disclosure are not sensitive to freezing and thawing and are stable when stored at higher temperatures than the compositions of the prior art. The increased stability of the present hybridization buffers cmay also support denaturation at temperatures above about 66° C., for example at about 80° C. Hybridization buffers of the present disclosure also exhibit lower viscosity than certain prior existing hybridization buffers and therefore facilitate mixing, pipetting and spreading in capillary fields such as the space between a slide and a slide cover.

In additional aspects, the present disclosure provides a hybridization composition comprising at least one nucleic acid sequence, sulfolane, polyvinyl sulfonic acid or a salt thereof, and one or more additional components. The additional component may be a buffering agent, salt, accelerating agent, chelating agent, detergent, blocking agent, or combination thereof.

The present disclosure also provides hybridization buffers that are easier to store and use due to increased homogeneity and increased stability. In some embodiments, the present hybridization buffers are stable when stored at higher temperatures than certain existing hybridization buffers, such as temperatures greater 0° C. The increased stability of the present hybridization buffers also supports hybridization methods that include steps such as high temperature denaturation. In some embodiments, hybridization buffers may also exhibit lower viscosity than certain existing hybridization buffers. These features of the present disclosure provide advantages in hybridization methods that include mixing, pipetting and spreading in capillary fields, among other advantages that will be recognized by the skilled artisan, when compared to certain existing hybridization buffers.

In certain preferred embodiments, the present disclosure provides hybridization compositions comprising at least one nucleic acid, sulfolane in a concentration of about 13% (v/v), polyvinyl sulfonic acid, or a salt thereof, in a concentration of about 30% (w/v), dextran sulfate in a concentration of about 10% (w/v), NaCl in a concentration of about 600 mM and MOPS in a concentration of about 40 mM.

According to yet another aspect, the present disclosure relates to the use of a hybridization buffer comprising sulfolane and PVSA or a salt thereof as described herein for use in hybridization protocol and assays, such as those described below.

DETAILED DESCRIPTION

Figure 1A:
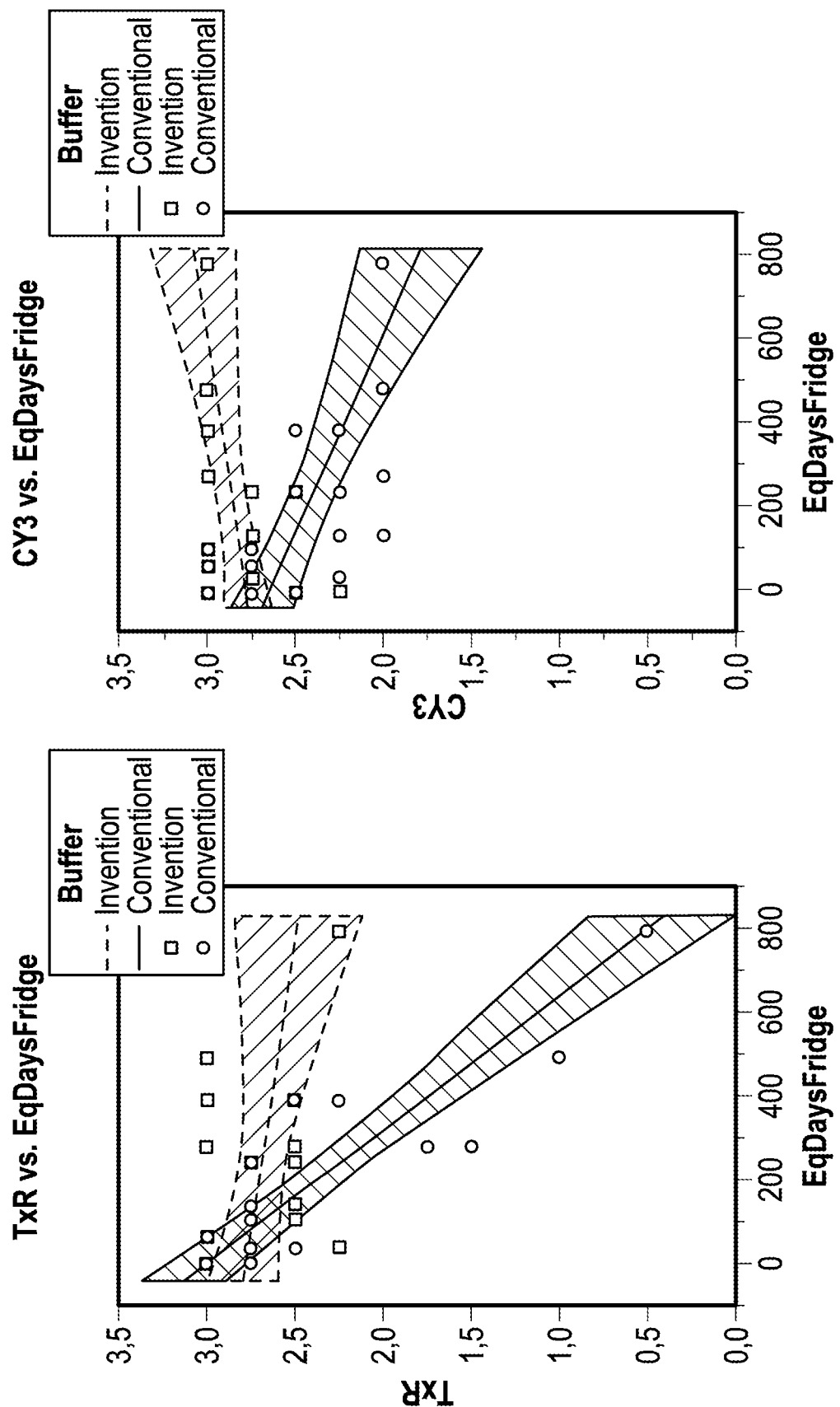
FIGS. 1A, 1B, and 1C provide a graphical representation demonstrating that the FISH hybridization buffers of the present disclosure are more stable than certain existing FISH buffers.

The present disclosure provides a hybridization buffer comprising a sulfone solvent and a polyvinyl sulfonic acid or a salt thereof. In some embodiments, the hybridization buffer further comprises water. The hybridization buffer is suitable for use in hybridization methods, such as in situ hybridization (ISH). ISH is a method used for visualization of genetic structures or genetic events that can be performed, in some embodiments on formalin-fixed paraffin-embedded tissue (FFPE), metaphase spreads, cytospins, histological smears or other biological material placed on glass slides. Labelled probes base-pair to target material such as DNA or RNA during the ISH staining process, and this allows for subsequent identification and quantification of relevant genetic information in the target material. Stained slides are, in some embodiments, inspected with fluorescent or brightfield microscopy, and interpretation of the gathered information can be used for diagnostic, prognostic or research purposes.

Therefore, ISH provides fast and precise description of genetic structures and events such as amplifications, deletions, translocations and chromosome copy number changes in the context of an undisrupted morphological structure. In some instances, links between genetic aberrations, their frequencies and specific cells harboring these changes can be retrieved by the practitioner.

In some embodiments, nucleic acid probes are combined with a hybridization buffer in a relevant concentration to form a hybridization composition. The hybridization composition is mixed and then used in the staining process as it provides a suitable environment for denaturation and hybridization of probes and target nucleotides in the biological material of interest. One important function of the hybridization composition is to lower the DNA melting temperature, thereby permitting hybridization at a reduced temperature which reduces tissue damage.

The present hybridization buffers provide several advantages over certain existing hybridization buffers. For instance, the hybridization buffers of the present disclosure provide, in certain embodiments, an ISH hybridization buffer with a lower viscosity (for example, a viscosity less than 1000 mPa·s at 25° C., or less than 100) than certain existing hybridization buffers. The lower viscosity associated with hybridization buffers of the present disclosure facilitates fast and robust spreading of the hybridization buffers in capillary fields. This is advantageous over previous hybridization buffers because slow, non-robust spreading in capillary fields formed between glass slides, for example, may leave airspaces where functionality of the hybridization buffer is absent. The lower viscosity exhibited by hybridization buffers of the present disclosure also provide greater ease in user handling with respect to pipetting and mixing where high viscosity buffers present challenges.

In addition, the hybridization buffers of the present disclosure provide improved homogeneity and long-term storage when compared to certain existing hybridization buffers. In some embodiments, hybridization buffers of the present disclosure can be stored long-term at 2-8° C. which provides a significant advantage over certain existing ISH hybridization buffers that generally must be stored at a temperature of −18° C. or lower. The present hybridization buffers do not solidify, do not form extensive precipitates and/or exhibit phase separation to the extent that many buffers do at such storage temperatures. Because the present hybridization buffers need not be stored at a temperature of −18° C. or lower, they need not be thawed, equilibrated to 20-25° C., and then extensively mixed to solubilize precipitates and homogenize liquid phases, nor do they need to be refrozen at temperatures below −18° C. after use. As a result, the present hybridization buffers avoid freeze-thaw damage. The hybridization buffers of the present disclosure provide advantages in ease of use because they do not need to be frozen for long-term storage and can instead be stored long-term at temperatures such as 2-8° C.

Certain existing hybridization buffers also exhibit inhomogeneity at low temperatures and in some instances, special attention to temperature equilibration and the mixing process is required. In some cases, a separate instrument, such as a Dako Omnis Mixing Device, need to be used for thawing and homogenization of probe products in certain existing hybridization buffers prior to use. However, the present hybridization buffers maintain homogeneity during long-term storage and no extra mixing steps or devices are required.

In addition, certain existing hybridization buffers exhibit instability. For example, buffers that utilize ethylene carbonate as the solvent may exhibit instability due to hydrolysis of ethylene carbonate. Ethylene carbonate hydrolysis is temperature dependent, and, accordingly, buffers that include ethylene carbonate are less desirable for use at temperatures above 66° C. However, the hybridization buffers provided by the present disclosure do not contain ethylene carbonate and are therefore more stable at high temperatures. For example, certain embodiments of the hybridization buffers provided by the present disclosure can be used at temperatures of 80° C.

In some embodiments, the present disclosure provides new hybridization buffers that can be used without a requirement for hardware-dependent mixing and with a reduced viscosity to ease automated and manual handling. The present hybridization buffers also exhibit improved solubility and stability. The stability of the hybridization buffers of the present disclosure provides acceptable long-term storage at 2-8° C. where they are homogeneous without phase separation or precipitation. Therefore, the present hybridization buffers do not require thorough mixing prior to use. Accordingly, hybridization buffers based on the present disclosure may be transferred directly from storage at 2-8° C. to the in-use situation.

The present hybridization buffers and compositions also exhibit a lower viscosity compared to certain existing ISH buffers. Without wishing to be bound by theory, the reduction in the concentration of the high molecular weight components, such as dextran sulfate (MW 500.000), is likely to be the primary reason for the reduced viscosity. Compositions and buffers of the present disclosure provide a viscosity reduction of up to 39% (at 25° C.) when compared to existing buffers. Without wishing to be bound by theory, addition of a synthetic sulfonate polymer, such as poly vinyl sulfonate sodium salt MW 3,000-10,000 (PVSA), to the present compositions is predicted to functionally counteract the decrease in dextran sulfate (MW 500,000) so that the present compositions continue to provide high quality staining results even at the lower viscosities. Again, without wishing to be bound by theory, the excellent performance and functionality of the compositions of the present disclosure are thought to have been maintained due to the addition of a synthetic sulfonate polymer, such as PVSA or a salt thereof.

In some embodiments, the hybridization buffers and compositions of the present disclosure include a sulfone solvent, such as sulfolane, instead of ethylene carbonate and other solvents that are present in certain existing hybridization buffers. Without wishing to be bound by theory, sulfolane is believed to have a very high chemical and thermal stability compared to ethylene carbonate, and therefore the hybridization buffers and compositions of the present disclosure can be stored at elevated storage temperatures (2-8° C.) and used at higher denaturation temperatures. The ability to employ higher denaturation temperatures in a hybridization protocol allows one to perform more efficient denaturation of target nucleic acids and hybridization compositions and/or the whole hybridization protocol in less time.

The hybridization buffers and compositions of the present disclosure also provide high quality staining signal-quality that is similar to the results obtained with commercially available hybridization buffers. Without wishing to be bound by theory, it is believed that the thermal stability of the present hybridization buffers and compositions allows them to be used at higher denaturation temperatures in accordance with the recommendation for ISH probes, such as SureFISH probes.

Table 1 provides a comparison between characteristics of various embodiments of the present hybridization buffers compared to certain existing hybridization buffers. It should be recognized that embodiments need not have all these characteristics, as having one or more can provide significant advantages over certain existing hybridization buffers.

TABLE 1

| | Present Hybridization Buffers | Certain Existing Hybridization Buffers |
|---|---|---|
| Homogeneity (at storage temperature) | Soluble/no phase separation | Insoluble / w. phase separation |
| Mixing prior to use | No mixing required | Required and hardware-dependent |
| Freeze thaws | Freeze-thaws not relevant | Up to 10 freeze-thaws allowed |

TABLE 1-continued

| | Present Hybridization Buffers | Certain Existing Hybridization Buffers |
|---|---|---|
| Chemical stability | Stable at relevant high temperature | Temperature-dependent degradation |
| Storage temperature | 2-8 °C. (expected) | ≤ −18 °C. |
| Viscosity | 39% reduction (approximately) | = 63 mPa.s |
| Spreading in capillary fields | Improved | Slow |
| Supporting high denaturation temperature (≥66 °C.) | Yes | No |

In the context of the present disclosure the following terms are to be understood as follows:

"Hybridization" refers to binding of a nucleic acid molecule or sequence to a complementary nucleic acid molecule or sequence. "Hybridization buffer" refers to compositions adapted for performing a hybridization protocol, for example, to facilitate binding of a nucleic acid probe to a target nucleic acid sequence. Hybridization buffers may comprise, e.g., at least one solvent, at least one accelerating agent, and water. "Hybridization compositions" refers to compositions comprising a hybridization buffer and at least one nucleic acid probe. It should be understood that the hybridization buffers and compositions of the current technology comprise additional components at various concentrations. Accordingly, unless specified otherwise, solvent concentrations of the hybridization buffers and compositions are provided herein in a volume by volume (v/v) basis while additional solid component concentrations are provided in weight by volume (w/v) basis.

"Hybridization process" generally refers to an action, time period, or portion of a larger method, in which conditions are provided for one nucleic acid to hybridize to another nucleic acid. A hybridization process can be understood as incorporating both denaturation and re-annealing in a hybridization procedure (such as when the procedure does not include a separate denaturation step) unless otherwise specified. "Hybridization protocol" means a method comprising a hybridization process and one or more other processes, such as preparatory or rinsing processes.

"Biological sample" is to be understood as any in vivo, in vitro, or in situ sample of one or more cells or cell fragments. This can, for example, be a unicellular or multicellular organism, tissue section, cytological sample, chromosome spread, purified nucleic acid sequences, artificially made nucleic acid sequences made by, e.g., a biologic based system or by chemical synthesis, microarray, or other form of nucleic acid chip. In one embodiment, a sample is a mammalian sample, such as, e.g., a human, murine, rat, feline, or canine sample.

"Nucleic acid," "nucleic acid chain," and "nucleic acid sequence" mean anything that binds or hybridizes using base pairing including, oligomers or polymers having a backbone formed from naturally occurring nucleotides and/or nucleic acid analogs comprising nonstandard nucleobases and/or nonstandard backbones (e.g., a peptide nucleic acid (PNA) or locked nucleic acid (LNA)), or any derivatized form of a nucleic acid.

As used herein, the term "peptide nucleic acid" or "PNA" means a synthetic polymer having a polyamide backbone with pendant nucleobases (naturally occurring and modified). The pendant nucleobase, such as, e.g., apurine or pyrimidine base on PNA may be connected to the backbone via a linker. In one embodiment, the PNA has an N-(2-aminoethyl)-glycine) backbone. PNAs may be synthesized (and optionally labeled) as taught in PCT/US02/30573, the disclosure of which is incorporated herein by reference in its entirety, or any of the references cited therein. PNAs hybridize tightly, and with high sequence specificity, with DNA and RNA, because the PNA backbone is uncharged. Thus, short PNA probes may exhibit comparable specificity to longer DNA or RNA probes. PNA probes may also show greater specificity in binding to complementary DNA or RNA. As used herein, the term "locked nucleic acid" or "LNA" means an oligomer or polymer comprising at least one or more LNA subunits. As used herein, the term "LNA subunit" means a ribonucleotide containing a methylene bridge that connects the 2'-oxygen of the ribose with the 4'-carbon. See generally, Kurreck, Eur. J. Biochem., 270: 1628-44 (2003), the disclosure of which is incorporated herein by reference in its entirety.

Examples of nucleic acids and nucleic acid analogs also include polymers of nucleotide monomers, including double and single stranded deoxyribonucleotides (DNA), ribonucleotides (RNA), anomeric forms thereof, synthetic and natural analogs thereof, and the like. The nucleic acid chain may be composed entirely of deoxyribonucleotides, ribonucleotides, peptide nucleic acids (PNA), locked nucleic acids (LNA), synthetic or natural analogs thereof, or mixtures thereof. DNA, RNA, or other nucleic acids as defined herein can be used in the methods and compositions of the present disclosure.

"Polar aprotic solvent" refers to an organic solvent having a dipole moment of about 2 debye units or more, a water solubility of at least about 5% (volume) at or near ambient temperature, i.e., about 20° C., and which does not undergo significant hydrogen exchange at approximately neutral pH, i.e., in the range of 5 to 9, or in the range 6 to 8.

"Aqueous solution" is to be understood as a solution containing water, even small amounts of water. For example, a solution containing 1% water is to be understood as an aqueous solution.

"Repetitive Sequences" is to be understood as referring to the rapidly reannealing (approximately 25%) and/or intermediately reannealing (approximately 30%) components of mammalian genomes.

"Non-toxic" and "reduced toxicity" are defined with respect to the toxicity of formamide. Formamide is toxic and may cause harm to the unborn child. In some embodiments, the hybridization buffers and compositions of the present technology do not contain formamide and are less toxic than certain existing hybridization buffers that contain formamide.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic. Such non-aromatic monocyclic hydrocarbons or bicyclic hydrocarbons that are completely saturated or that contain one or more units of unsaturation are also referred to herein as "carbocycle", "cycloaliphatic" or "cycloalkyl". An aliphatic group generally has may have one point of attachment to the rest of a molecule, though it can have more than one point of attachment, such as when it is a linker within the molecule. In some embodiments, aliphatic groups contain 1-6 aliphatic carbon atoms, though an aliphatic group may have one or more substituents having additional carbon atoms.

Sulfone solvents for use in the present hybridization buffers, compositions and methods include sulfolane and other solvents having sulfone functionality. In some embodiments, the sulfone solvent may be selected from the group consisting of: dimethyl sulfone, diphenyl sulfone, methyl phenyl sulfone, tetramethylene sulfone (sulfolane), and mixtures thereof. In some embodiments, the sulfone solvent is a cyclic sulfone component such as sulfolane. One aspect of the present disclosure are hybridization buffers or hybridization compositions for use in hybridization. In some embodiments, the hybridization buffers may comprise an aqueous composition. Some embodiments relate to hybridization compositions comprising a hybridization buffer and at least one nucleic acid probe. In some embodiments, the hybridization buffer comprises at least one sulfone solvent in an amount effective to facilitate hybridization of a nucleic acid probe to a target nucleic acid sequence. An amount effective to facilitate hybridization of a nucleic acid probe to a target nucleic acid sequence is an amount that enables hybridization at a level usable for the intended purpose. For example, one way to test for whether the amount of sulfone solvent is effective to enable hybridization is to determine whether the sulfone solvent, when used in the hybridization methods and compositions described herein, yields a detectable signal.

Non-limiting examples of effective amounts of sulfone solvents include, e.g., about 1% to about 95% (v/v). In some embodiments, the concentration of sulfone solvent is 5% to 60% (v/v); or 10% to 60% (v/v). In still other embodiments, the concentration of sulfone solvent is 1% to 50%, 5% to 30%, 10% to 20%, 10% to 30%, or 10% to 25% (v/v) are also suitable. In some embodiments, the sulfone solvent will be present at a concentration of at least about 0.1%, 0.25%, 0.5%, 1%, 2%, 3%, 4%, 5%, 7.5%, 10%, 11%, 12% or 13% (v/v). In other embodiments, the sulfone solvent will be present at a concentration of at most 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% (v/v). It is expressly contemplated that any of the foregoing minimum and maximum values may be combined to form a range. It is also expressly contemplated that any concentration between the minimum and maximum values in a range may be used.

The present hybridization buffers comprise a sulfonic acid polymer or salt thereof. In some embodiments, the sulfonic acid polymer is of general formula (I):

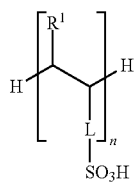

or a salt thereof, wherein: $R^1$ is hydrogen or $C_{1-6}$ aliphatic; L is a covalent bond or $C_{1-6}$ aliphatic; and n is an integer greater than 10. In some embodiments, $R^1$ is hydrogen. In some embodiments, $R^1$ is $C_{1-6}$ aliphatic. In some embodiments, L is a covalent bond. In some embodiments, L is $C_{1-6}$ aliphatic. In some embodiments, L is methylene. In some embodiments, the sulfonic acid polymer or salt thereof is of general formula (Ia):

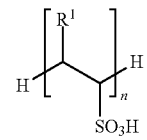

or a salt thereof, wherein: $R^1$ is hydrogen or $C_{1-6}$ aliphatic. In some embodiments, the sulfonic acid polymer or salt thereof is polyvinylsulfonic acid or a salt thereof. In some embodiments, the sulfonic acid polymer or salt thereof is related to polyantholesulfonic acid and is of general formula (II):

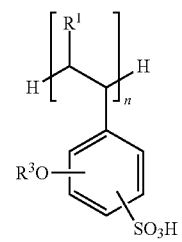

or a salt thereof, wherein: $R^1$ is hydrogen or $C_{1-6}$ aliphatic; $R^3$ is hydrogen or $C_{1-6}$ alkyl; and n is an integer greater than 10.

In some embodiments, the sulfonic acid polymer or salt thereof is of general formula (IIa):

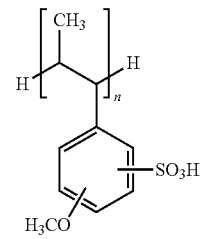

or a salt thereof. In some embodiments, the sulfonic acid polymer or salt thereof is polyantholesulfonic acid or a salt thereof.

In any one of the aforementioned embodiments, n may be an integer from 10 to 200, from 10 to 150, from 10 to 100, from 10 to 90, from 10 to 80, from 10 to 70, from 20 to 150, from 30 to 150, from 40 to 150, from 50 to 150, from 60 to 150, from 70 to 150, from 80 to 150, from 90 to 150, from 100 to 150, from 50 to 120, from 60 to 120, from 70 to 120, from 80 to 120, from 90 to 120, etc.

In any one of the aforementioned embodiments, the sulfonic acid polymer or salt thereof may have an average molecular weight in the range from about 500 to about 1,000 Da, about 1,000 to about 2,000 Da, about 2,000 to about 4,000 Da, about 3,000 to about 5,000 Da, about 4,000 to about 6,000 Da, about 5,000 to about 7,000 Da, about 6,000 to about 8,000 Da, about 7,000 to about 9,000 Da, about 8,000 to about 10,000 Da, about 2,000 to about 20,000 Da, about 3,000 to about 20,000 Da, about 4,000 to about 20,000 Da, about 5,000 to about 20,000 Da, about 6,000 to about 20,000 Da, about 7,000 to about 20,000 Da, about 2,000 to about 9,000 Da, about 3,000 to about 9,000 Da, about 4,000 to about 9,000 Da, about 5,000 to about 9,000 Da, about 6,000 to about 9,000 Da, about 7,000 to about 9,000 Da, or about 8,000 to about 9,000 Da. In some embodiments, the average molecular weight is less than about 1,000 Da, less than about 2,000 Da, less than about 3,000 Da, less than about 4,000 Da, less than about 5,000 Da, less than about 6,000 Da, less than about 7,000 Da, less than about 8,000 Da, less than about 9,000 Da, less than about 10,000 Da, or less than about 20,000 Da. It is expressly contemplated that any of the foregoing minimum and maximum values may be combined to form a range. It is also expressly contemplated that any average molecular weight between the minimum and maximum values in a range may be used.

As demonstrated in the examples, sulfonic acid polymers of lower molecular weight performed better than other higher molecular anionic polymers. Thus, in some embodiments, the sulfonic acid polymer or salt thereof is of general formula (III):

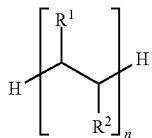

wherein: $R^1$ is hydrogen or $C_{1-6}$ aliphatic; $R^2$ is a covalent bond, $C_{1-6}$ aliphatic, phenyl, or a 6-membered heteroaryl ring having 1-3 nitrogens, wherein: $R^2$ is substituted with 1 or 2-$SO_3H$ groups or a salt thereof, provided that when $R^2$ is a covalent bond, only 1-$SO_3H$ group or a salt thereof is present, and $R^2$ is optionally substituted with 1-2 groups independently selected from —$R^3$, halogen, —CN, —$NO_2$, —$OR^3$, —$N(R^3)_2$, and —$SR^3$, wherein each $R^3$ is independently hydrogen or a $C_{1-6}$ alkyl group; and n is an integer greater than 10, preferably up to an integer such that the sulfonic acid polymer or salt thereof has an average molecular weight within the ranges set forth herein.

In some embodiments, the sulfonic acid polymer or salt thereof of formula (III) has an average molecular weight in the range from about 500 to about 1,000 Da, about 1,000 to about 2,000 Da, about 2,000 to about 4,000 Da, about 3,000 to about 5,000 Da, about 4,000 to about 6,000 Da, about 5,000 to about 7,000 Da, about 6,000 to about 8,000 Da, about 7,000 to about 9,000 Da, about 8,000 to about 20,000 Da, about 2,000 to about 20,000 Da, about 3,000 to about 20,000 Da, about 4,000 to about 20,000 Da, about 5,000 to about 20,000 Da, about 6,000 to about 20,000 Da, about 7,000 to about 20,000 Da, about 2,000 to about 9,000 Da, about 3,000 to about 9,000 Da, about 4,000 to about 9,000 Da, about 5,000 to about 9,000 Da, about 6,000 to about 9,000 Da, about 7,000 to about 9,000 Da, or about 8,000 to about 9,000 Da. In some embodiments, the average molecular weight is less than about 1,000 Da, less than about 2,000 Da, less than about 3,000 Da, less than about 4,000 Da, less than about 5,000 Da, less than about 6,000 Da, less than about 7,000 Da, less than about 8,000 Da, less than about 9,000 Da, less than about 10,000 Da, or less than about 20,000 Da. It is expressly contemplated that any of the foregoing minimum and maximum values may be combined to form a range. It is also expressly contemplated that any average molecular weight between the minimum and maximum values in a range may be used.

In some embodiments, n in general formula (III) may be an integer from 10 to 200, from 10 to 150, from 10 to 100, from 10 to 90, from 10 to 80, from 10 to 70, from 20 to 150, from 30 to 150, from 40 to 150, from 50 to 150, from 60 to 150, from 70 to 150, from 80 to 150, from 90 to 150, from 100 to 150, from 50 to 120, from 60 to 120, from 70 to 120, from 80 to 120, from 90 to 120, etc.

The concentration of the sulfonic acid polymer in the hybridization buffer can impact the hybridization rate of the nucleic acids in the assay. In some embodiments, the concentration of the polymer in the hybridization buffer is between about 0.1 and about 40%, between about 0.2% and about 15%, between about 0.2% and about 10%, between about 0.2% and about 9%, between about 0.2% and about 8%, between about 0.2% and about 7%, between about 0.2% and about 6%, between about 0.2% and about 6%, between about 0.5% and about 5%, between about 1% and about 5%, between about 1% and about 4%, between about 0.5% and about 4%, between about 0.5% and about 3%, between about 1% and about 2.5%, between about 5% to about 40%, between about 10% to about 35%, between about 15% to about 30%, or between about 25% to about 35% weight by volume. It is expressly contemplated that any of the foregoing minimum and maximum values may be combined to form a range. It is also expressly contemplated that any concentration between the minimum and maximum values in a range may be used.

The present hybridization buffers may contain various other components known in the art or later developed. For example, the hybridization buffer may contain one or more of the following components: buffering agents, accelerating agents, chelating agents, salts, detergents, and blocking agents.

In some embodiments, the hybridization buffer includes NaCl as the salt. NaCl may be present in the hybridization buffer at a concentration of from about 1 mM to about 1200 mM. In some embodiments, the hybridization buffer contains NaCl at a concentration of about 600 mM. In some embodiments, the hybridization buffer includes 3-(N-morpholino)propanesulfonic acid (MOPS) as the buffering agent. MOPS may be present in the hybridization buffer at a concentration from about 1 mM to about 50 mM and at the pH of about 6.0 to about 8.0. In particular embodiments, the hybridization buffer contains MOPS at a concentration of about 40 mM at a pH of about 7.2.

For example, the present hybridization buffers may comprise one or more buffering agents. In some embodiments, the buffering agent is selected from 3-morpholinopropane-1-sulfonic acid (MOPS), SSC, 2-[4-(2-hydroxyethyl)piperazin-1-yl]ethanesulfonic acid (HEPES), SSPE, PIPES, TMAC, TRIS, SET, citric acid, phosphate buffer, such as, e.g., potassium phosphate, sodium phosphate, or sodium pyrophosphate, and combinations thereof. The buffering agents may be present at concentrations from 0.5× to 50×. Typically, the buffering agents are present at concentrations from about 2× to about 10×. Concentrations of buffering agents may be adjusted in the range of about 1 mM to about 500 mM as required to stabilize the hybridization buffers and compositions of the present technology at a near neutral pH.

The present hybridization buffers may comprise one or more accelerating agents. In some embodiments, the accelerating agent is selected from polymers such as FICOLL, PVP, heparin, dextran, and dextran sulfate; proteins such as BSA; glycols such as ethylene glycol, glycerol, 1,3 propanediol, propylene glycol, polyethylene glycol, or diethylene glycol, and combinations thereof. For instance, the hybridization buffers s can include such as Denhardt's solution and BLOTTO, and organic solvents such as formamide, dimethylformamide, DMSO, etc. The accelerating agent may be present at concentrations from about 1% to about 80%. Typically, formamide is present at concentrations from about 1% to about 75%, or about 25% to about 75% volume by volume in certain embodiments. DMSO, dextran sulfate, and glycol are present at concentrations from about 5% to about 20%. It will be appreciated that other concentrations of dextran sulfate may be used depending on the molecular weight of the dextran sulfate. In certain embodiments, the hybridization buffer contains about 5% to about 20% (w/v) dextran sufate. In some embodiments, the hybridization buffer contains less than about 10% (v/v) formamide. In other embodiments, the hybridization buffer does not contain formamide.

In some embodiments, the hybridization buffers of the present disclosure include dextran sulfate (DS) in a concentration lower than those of traditional hybridization buffers. In some embodiments, the concentration of dextran sulfate is no greater than about 20% (w/v), alternatively no greater than about 15% (w/v), alternatively no greater than about 10% (w/v). In still other embodiments, the concentration of dextran sulfate is from about 1% to about 20%, alternatively from about 5% to about 15% (w/v). In some embodiments, dextran sulfate will be present at a concentration of about 0.1%, about 0.25%, about 0.5%, about 1%, about 2%, about 3%, about 4%, or about 5% (w/v). In other embodiments, dextran sulfate will be present at a concentration of about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20% (w/v). It is expressly contemplated that any of the foregoing values may be combined to form a range. In certain embodiments, hybridization buffers of the present disclosure include dextran sulfate at a concentration of about 10% (w/v).

The present hybridization buffers may comprise one or more chelating agents. In some embodiments, the chelating agent is selected from EDTA, EGTA, or others. The chelating agents may be present at concentrations from about 0.1 mM to about 10 mM, alternatively from about 0.5 mM to about 5 mM.

The present hybridization buffers may comprise one or more salts. In some embodiments, the salt is selected from sodium chloride, sodium phosphate, magnesium phosphate, etc. The salts may be present at concentrations from about 1 mM to about 1200 mM or any concentration between these endpoints. Typically, the salts are present at concentrations from about 10 mM to about 500 mM or any concentration between these endpoints.

The present hybridization buffers may comprise one or more detergents. The detergents may include Tween, SDS, Triton, CHAPS, deoxycholic acid, etc. The detergent may be present at concentrations from about 0.01% to about 10%, alternatively from about 0.1% to about 1% (w/v) or any concentration between these endpoints.

The present hybridization buffers may comprise one or more nucleic acid blocking agents, such as yeast tRNA, homopolymer DNA, denatured salmon sperm DNA, herring sperm DNA, total human DNA, COT1 DNA, etc. The blocking nucleic acids may be present at concentrations of about 0.05 mg/mL to about 100 mg/mL or any concentration between these two endpoints.

If the present hybridization buffers comprise accelerating agents such as dextran sulfate, glycol, or DMSO, the dextran sulfate may be present in concentrations no greater than about 20% (w/v) (alternatively, no greater than about 15% or about 10%), the glycol may be present at concentrations of from about 0.1% to about 10% or any concentration between these two endpoints, and the DMSO may be from about 0.1% to about 10% or any concentration between these two endpoints. In some embodiments, the hybridization buffer does not comprise DMSO as an accelerating agent. In some embodiments, the hybridization buffer does not comprise formamide, or comprises formamide with the proviso that the hybridization buffer contains less than about 10%, or less than about 5%, or less than about 2%, or less than about 1%, or less than about 0.5%, or less than about 0.1%, or less than about 0.05%, or less than about 0.01% formamide.

If the present hybridization buffers comprise citric acid, the concentrations may range from about 1 mM to about 50 mM and the pH may range from about 5.0 to about 8.0 or any concentrations between these endpoints. In some embodiments, the concentration of citric acid may be about 10 mM and the pH may be about 6.2.

The present hybridization buffers may comprise agents that reduce non-specific binding to, for example, the cell membrane, such as salmon sperm or small amounts of total human DNA or, for example, they may comprise blocking agents to block binding of, e.g., repeat sequences to the target such as larger amounts of total human DNA or repeat enriched DNA or specific blocking agents such as PNA or LNA fragments and sequences. These agents may be present at concentrations of from about 0.01 µg/µL to about 100 µg/µL or about 0.01 µM to about 100 µM or any concentrations between these endpoints. For example, in some embodiments, these agents will be about 0.1 µg/µL total human DNA, or about 0.1 µg/µL non-human DNA, such as herring sperm, salmon sperm, or calf thymus DNA, or about 5 µM blocking PNA.

If the present hybridization buffers are used in a hybridization assay, they may further comprise one or more nucleic acid probes to form a hybridization composition. The probes may be directly or indirectly labeled with detectable compounds such as enzymes, chromophores, fluorochromes, and haptens. The DNA probes may be present at concentrations of about 0.1 ng/µL to about 100 ng/µL. For example, in some embodiments, the probes may be present at concentrations of about 1 ng/µL to about 10 ng/µL. The PNA probes may be present at concentrations of about 0.5 nM to about 5000 nM. For example, in some embodiments, the probes may be present at concentrations of about 5 nM to about 1000 nM.

In one embodiment, a hybridization buffer comprises a mixture of 13% sulfone solvent (v/v) (e.g., sulfolane), 10% dextran sulfate (w/v), 30% polyvinyl sulfonic acid or a salt thereof (w/v), 600 mM NaCl, 40 mM MOPS buffer pH 7.2. Another exemplary hybridization buffer of the present disclosure comprises a mixture of 14% (v/v) sulfone solvent (e.g., sulfolane), 10% dextran sulfate (w/v), 30% polyvinyl sulfonic acid (w/v), 600 mM NaCl, 40 mM MOPS buffer pH 7.2, and 0.1 µg/µL total human DNA. Yet another exemplary hybridization buffer comprises 15% polar aprotic solvent (v/v) (e.g., sulfolane), 10% dextran sulfate (w/v), 30% polyvinyl sulfonic acid or salt thereof (w/v), 600 mM NaCl, 40 mM MOPS buffer pH 7.2, and 0.1 µg/µL non-human DNA (e.g., herring sperm, salmon sperm, or calf thymus) or 0.5% formamide or 1% glycol (e.g., ethylene glycol, 1,3 propanediol, or glycerol).

In some embodiments, the sulfone solvent is the only polar aprotic solvent present in the hybridization buffer. In other embodiments, the present hybridization buffers comprise one or more other or secondary polar aprotic solvents.

In some embodiments, the present hybridization buffers comprise one or more additional solvents (in addition to sulfolane). For instance, the hybridization buffers may comprise one or more polar aprotic solvents such as solvents having lactone, nitrile, sulfite, and/or carbonate functionality. Such solvents are distinguished by their relatively high dielectric constants, high dipole moments, and solubility in water. An exemplary polar aprotic solvent with lactone functionality is γ-butyrolactone (GBL), an exemplary polar aprotic solvent with nitrile functionality is acetonitrile (AN), an exemplary polar aprotic solvent with sulfite functionality is glycol sulfite/ethylene sulfite (GS), and an exemplary polar aprotic solvents with carbonate functionality are ethylene carbonate (EC), propylene carbonate (PC), or ethylene trithiocarbonate (ETC). Different polar aprotic solvents may impart different properties on the hybridization buffers. For example, the choice of polar aprotic solvent may contribute to the stability of the hybridization buffer, since certain polar aprotic solvents may degrade over time. For example, the polar aprotic solvent ethylene carbonate breaks down into ethylene glycol, which is a relatively stable molecule, and carbon dioxide, which can interact with water to form carbonic acid, altering the acidity of the hybridization buffers. Without being bound by theory, it is believed that the change in pH upon breakdown of ethylene carbonate makes hybridization buffers less effective for hybridization. Accordingly, in some embodiments, the present hybridization buffers are substantially free of ethylene carbonate, or of polar aprotic solvents having carbonate functionality.

However, for example, hybridization buffers of the present disclosure that contain sulfolane, dextran sulfate and PVSA or a salt thereof are stable and homogeneous when stored at 2-8° C. for approximately 12 months. For example, a hybridization buffer containing sulfolane in a concentration of about 13% (v/v), polyvinyl sulfonic acid in a concentration of about 30% (w/v), dextran sulfate in a concentration of about 10% (w/v), NaCl in a concentration of about 600 mM and MOPS buffer pH 7.2 in a concentration of about 40 mM provides a homogeneous solution that can be stored at 2-8° C. and used with minimal mixing.

According to another aspect of the present disclosure, some embodiments of the present hybridization buffers have reduced toxicity compared to traditional hybridization buffers. For example, a less-toxic hybridization buffer than traditional hybridization solutions may comprise a hybridization buffer as described herein with the proviso that the hybridization buffer does not contain formamide, or with the proviso that the hybridization buffer contains less than about 10%, or less than about 5%, or less than about 2%, or less than about 1%, or less than about 0.5%, or less than about 0.1%, or less than about 0.05%, or less than about 0.01% formamide. Other embodiments of the present disclosure may also comprise a hybridization buffer with the proviso that the hybridization buffer does not contain dimethyl sulfoxide (DMSO), or with the proviso that the hybridization buffer contains less than about 10%, about 5%, about 2%, or less than about 1%, or less than about 0.5%, or less than about 0.1%, or less than about 0.05%, or less than about 0.01% DMSO.

In some embodiments, the present hybridization methods and hybridization buffers are useful for the in vivo or in vitro analysis of genomic DNA, chromosomes, chromosome fragments, genes, and chromosome aberrations such as translocations, deletions, amplifications, insertions, mutations, or inversions associate with a normal condition or a disease. Further, the methods and hybridization buffers are useful for detection of infectious agents as well as changes in levels of expression of RNA, e.g., mRNA and its complementary DNA (cDNA).

Other uses include the in vivo or in vitro analysis of messenger RNA (mRNA), viral RNA, viral DNA, small interfering RNA (siRNA), small nuclear RNA (snRNA), noncoding RNA (ncRNA, e.g., tRNA and rRNA), transfer messenger RNA (tmRNA), micro RNA (miRNA), piwi-interacting RNA (piRNA), long noncoding RNA, small nucleolar RNA (snoRNA), antisense RNA, double-stranded RNA (dsRNA), methylations and other base modifications, single nucleotide polymorphisms (SNPs), copy number variations (CNVs), and nucleic acids labeled with, e.g., radioisotopes, fluorescent molecules, biotin, digoxigenin (DIG), or antigens, alone or in combination with unlabeled nucleic acids.

The present hybridization methods and hybridization buffers are useful for in vivo or in vitro analysis of nucleic acids using techniques such as northern blot, Southern blot, flow cytometry, autoradiography, fluorescence microscopy, chemiluminescence, immunohistochemistry, virtual karyotype, gene assay, DNA microarray (e.g., array comparative genomic hybridization (array CGH), gene expression profiling, Gene ID, Tiling array, gel electrophoresis, capillary electrophoresis, and in situ hybridizations such as FISH, SISH, CISH. The present methods and hybridization buffers may be used on in vitro and in vivo samples such as bone marrow smears, blood smears, paraffin embedded tissue preparations, enzymatically dissociated tissue samples, bone marrow, amniocytes, cytospin preparations, imprints, etc.

The present hybridization buffers can be varied for a particular application. For example, the concentration of sulfone solvent, salt, accelerating agent, blocking agent, and/or hydrogen ions (i.e. pH) may be varied in order to improve results for a particular application. For example, the concentration of sulfone solvent may be varied in order to improve signal intensity and background staining. Generally, as the concentration of solvent increases, signal intensity increases and background staining decreases.

In addition, the types of probes used in the present hybridization compositions may be varied to improve results. For example, in some aspects of the present disclosure, combinations of DNA/DNA probes may show less background than combinations of DNA/PNA probes in the present hybridization compositions. On the other hand, PNA probes tend to show stronger signals than DNA probes under low salt and/or low polar aprotic solvent concentrations. In fact, PNA probes also show signals when no sulfolane is present, whereas DNA probes show weak or no signals without sulfolane.

The present methods and hybridization buffers may be used fully or partly in all types of hybridization applications in the fields of cytology, histology, or molecular biology. According to one embodiment, the first or the second nucleic acid sequence is present in a biological sample. Examples of such samples include, e.g., tissue samples, cell preparations, cell fragment preparations, and isolated or enriched cell component preparations. The sample may originate from various tissues such as, e.g., breast, lung, colorectal, prostate, lung, head & neck, stomach, pancreas, esophagus, liver, and bladder, or other relevant tissues and neoplasia thereof: any cell suspension, blood sample, fine needle aspiration, ascites fluid, sputum, peritoneum wash, lung wash, urine, feces, cell scrape, cell smear, cytospin or cytoprep cells.

The sample may be isolated and processed using standard protocols. Cell fragment preparations may, e.g., be obtained by cell homogenizing, freeze-thaw treatment or cell lysing.

The isolated sample may be treated in many different ways depending of the purpose of obtaining the sample and depending on the routine at the site. Often the sample is treated with various reagents to preserve the tissue for later sample analysis, alternatively the sample may be analyzed directly. Examples of widely used methods for preserving samples are formalin-fixation followed by paraffin-embedding and cryo-preservation.

For metaphase spreads, cell cultures are generally treated with colcemid, or anther suitable spindle pole disrupting agent, to stop the cell cycle in metaphase. The cells are then fixed and spotted onto microscope slides, treated with formaldehyde, washed, and dehydrated in ethanol. Probes are then added, and the samples are analyzed by any of the techniques discussed below.

Cytology involves the examination of individual cells and/or chromosome spreads from a biological sample. Cytological examination of a sample begins with obtaining a specimen of cells, which can typically be done by scraping, swabbing or brushing an area, as in the case of cervical specimens, or by collecting body fluids, such as those obtained from the chest cavity, bladder, or spinal column, or by fine needle aspiration or fine needle biopsy, as in the case of internal tumors. In a conventional manual cytological preparation, the sample is transferred to a liquid suspending material and the cells in the fluid are then transferred directly or by centrifugation-based processing steps onto a glass microscope slide for viewing. In a typical automated cytological preparation, a filter assembly is placed in the liquid suspension and the filter assembly both disperses the cells and captures the cells on the filter. The filter is then removed and placed in contact with a microscope slide. The cells are then fixed on the microscope slide before analysis by any of the techniques discussed below.

In a traditional hybridization protocol using a cytological sample, slides containing the specimen are immersed in a formaldehyde buffer, washed, and then dehydrated in ethanol. The probes are then added and the specimen is covered with a coverslip. The slide is incubated at a temperature sufficient to denature any nucleic acid in the specimen (e.g., 5 minutes at 82° C.) and then incubated at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

Histology involves the examination of cells in thin slices of tissue. To prepare a tissue sample for histological examination, pieces of the tissue are fixed in a suitable fixative, typically an aldehyde such as formaldehyde or glutaraldehyde, and then embedded in melted paraffin wax. The wax block containing the tissue sample is then cut on a microtome to yield thin slices of paraffin containing the tissue, typically from 2 to 10 microns thick. The specimen slice is then applied to a microscope slide, air dried, and heated to cause the specimen to adhere to the glass slide. Residual paraffin is then dissolved with a suitable solvent, typically xylene, toluene, Clearify, Histo-Clear or others. These so-called deparaffinizing solvents are then removed with a washing-dehydrating type reagent prior to analysis of the sample by any of the techniques discussed below. Alternatively, slices may be prepared from frozen specimens, fixed briefly in 10% formalin or other suitable fixative, and then infused with dehydrating reagent prior to analysis of the sample.

In a traditional hybridization experiment using a histological sample, formalin-fixed paraffin embedded tissue specimens are cut into sections of 2-6 μm and collected on slides. The paraffin is melted (e.g., 30-60 minutes at 60° C.) and then removed (deparaffinated) by washing with xylene (or a xylene substitute), e.g., 2×5 minutes. The samples are rehydrated, washed, and then pre-treated (e.g., 10 minutes at 95-100° C.). The slides are washed and then treated with pepsin or another suitable permeabilizer, e.g., 3-15 minutes at 37° C. The slides are washed (e.g., 2×3 minutes), dehydrated, and probe is applied. The specimens are covered with a coverslip and the slide is incubated at a temperature sufficient to denature any nucleic acid in the specimen (e.g. 5 minutes at 82° C.), followed by incubation at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

The compositions and methods of the present disclosure can be used fully or partly in all types of nucleic acid hybridization techniques known in the art for cytological and histological samples. Such techniques include, for example, in situ hybridization (ISH), fluorescent in situ hybridization (FISH; including multi-color FISH, Fiber-FISH, etc.), chromogenic in situ hybridization (CISH), silver in situ hybridization (SISH), comparative genome hybridization (CGH), chromosome paints, and arrays in situ.

Molecular probes that are suitable for use in the present hybridization methods and compositions are described, e.g., in U. S. Patent Publication No. 2005/0266459, which is incorporated herein by reference in its entirety. In general, probes may be prepared by chemical synthesis or by amplifying a specific DNA sequence by cloning, inserting the DNA into a vector, and amplifying the vector an insert in appropriate host cells. Commonly used vectors include bacterial plasmids, cosmids, bacterial artificial chromosomes (BACs), PI diverted artificial chromosomes (PACs), or yeast artificial chromosomes (YACs). The amplified DNA is then extracted, purified and labeled for use as a probe. Methods for preparing and/or synthesizing probes are known in the art, e.g., as disclosed in PCT/US02/30573, the disclosure of which is incorporated herein by reference in its entirety.

In general, the type of probe determines the type of feature one may detect in a hybridization assay. For example, total nuclear or genomic DNA probes can be used as a species-specific probe. Chromosome paints are collections of DNA sequences derived from a single chromosome type and can identify that specific chromosome type in metaphase and interphase nuclei, count the number of a certain chromosome, show translocations, or identify extra-chromosomal fragments of chromatin. Different chromosomal types also have unique repeated sequences that may be targeted for probe hybridization, to detect and count specific chromosomes. Large insert probes may be used to target unique single-copy sequences. With these large probes, the hybridization efficiency is inversely proportional to the probe size. Smaller probes can also be used to detect aberrations such as deletions, amplifications, inversions, duplications, and aneuploidy. For example, differently-colored locus-specific probes can be used to detect translocations via split-signal in situ hybridization.

In general, the ability to discriminate between closely related sequences is inversely proportional to the length of the hybridization probe because the difference in thermal stability decreases between wild type and mutant complexes as probe length increases. Probes of greater than 10 hp in length are generally required to obtain the sequence diversity necessary to correctly identify a unique organism or clinical condition of interest. On the other hand, sequence differences as subtle as a single base (point mutation) in very short oligomers (<10 base pairs) can be sufficient to enable the discrimination of the hybridization to complementary nucleic acid target sequences as compared with non-target sequences.

In one embodiment, at least one set of the in situ hybridization probes may comprise one or more PNA probes, as defined above and as described in U.S. Pat. No. 7,105,294, disclosure of which is incorporated herein by reference in its entirety. Methods for synthesizing PNA probes are described in PCT/US02/30573, the disclosure of which is incorporated herein by reference in its entirety. Alternatively, or in addition, at least one set of the hybridization probes in any of the techniques discussed above may comprise one or more locked nucleic acid (LNA) probes, as described in WO 99/14226, the disclosure of which is incorporated herein by reference in its entirety. Due to the additional bridging bond between the 2' and 4' carbons, the LNA backbone is pre-organized for hybridization. LNA/DNA and LNA/RNA interactions are stronger than the corresponding DNA/DNA and DNA/RNA interactions, as indicated by a higher melting temperature. Thus, the present compositions and methods, which decrease the energy required for hybridization, are particularly useful for hybridizations with LNA probes.

In one embodiment, the probes may comprise a detectable label (a molecule that provides an analytically identifiable signal that allows the detection of the probe-target hybrid), as described in U.S. Patent Publication No. 2005/0266459, the disclosure of which is incorporated herein by reference in its entirety. The detectable label may be directly attached to a probe, or indirectly attached to a probe, e.g., by using a linker. Any labeling method known to those in the art, including enzymatic and chemical processes, can be used for labeling probes used in the present methods and compositions. In other embodiments, the probes are not labeled.

In general, in situ hybridization techniques such as CGH, FISH, CISH, and SISH, employ large, mainly unspecified, nucleic acid probes that hybridize with varying stringency to genes or gene fragments in the chromosomes of cells. Using large probes renders the in situ hybridization technique very sensitive. However, the successful use of large genomic probes in traditional hybridization assays depends on blocking the undesired background staining derived from, e.g., repetitive sequences that are present throughout the genome. Such blocking steps are time-consuming and expensive. As discussed below, the present methods and hybridization buffers advantageously reduce and/or eliminate the need for such blocking steps. However, in one embodiment, repetitive sequences may be suppressed according to the methods known in the art, e.g., as disclosed in PCT/US02/30573, the disclosure of which is incorporated herein by reference in its entirety.

Bound probes may be detected in cytological and histological samples either directly or indirectly with fluorochromes (e.g., FISH), organic chromogens (e.g., CISH), silver particles (e.g., SISH), or other metallic particles (e.g., gold-facilitated fluorescence in situ hybridization, GOLD-FISH). Thus, depending on the method of detection, populations of cells obtained from a sample to be tested may be visualized via fluorescence microscopy or conventional brightfield light microscopy.

Hybridization assays on cytological and histological samples are important tools for determining the number, size, and/or location of specific DNA sequences. For example, in CGH, whole genomes are stained and compared to normal reference genomes for the detection of regions with aberrant copy number. Typically, DNA from subject tissue and from normal control tissue is labeled with different colored probes. The pools of DNA are mixed and added to a metaphase spread of normal chromosomes (or to a microarray chip, for array- or matrix-CGH). The ratios of colors are then compared to identify regions with aberrant copy number.

FISH is typically used when multiple color imaging is required and/or when the protocol calls for quantification of signals. The technique generally entails preparing a cytological sample, labeling probes, denaturing target chromosomes and the probe, hybridizing the probe to the target sequence, and detecting the signal. Typically, the hybridization reaction fluorescently stains the targeted sequences so that their location, size, or number can be determined using fluorescence microscopy, flow cytometry, or other suitable instrumentation. DNA sequences ranging from whole genomes down to several kilobases can be studied using FISH. FISH may also be used on metaphase spreads and interphase nuclei.

FISH has been used successfully for mapping repetitive and single-copy DNA sequences on metaphase chromosomes, interphase nuclei, chromatin fibers, and naked DNA molecules, and for chromosome identification and karyotype analysis through the localization of large repeated families, typically the ribosomal DNAs and major tandem array families. One of the most important applications for FISH has been in detecting single-copy DNA sequences, in particular disease related genes in humans and other eukaryotic model species, and the detection of infections agents. FISH may be used to detect, e.g., chromosomal aneuploidy in prenatal diagnoses, hematological cancers, and solid tumors; gene abnormalities such as oncogene amplifications, gene deletions, or gene fusions; chromosomal structural abnormalities such as translocations, duplications, insertions, or inversions; contiguous gene syndromes such as microdeletion syndrome; the genetic effects of various therapies; viral nucleic acids in somatic cells and viral integration sites in chromosomes; etc. In multi-color FISH, each chromosome is stained with a separate color, enabling one to determine the normal chromosomes from which abnormal chromosomes are derived. Such techniques include multiplex FISH (m-FISH), spectral karyotyping (SKY), combined binary ration labeling (COBRA), color-changing karyotyping, cross-species color banding, high resolution multicolor banding, telomeric multiplex FISH (TM-FISH), split-signal FISH (ssFISH), and fusion-signal FISH.

CISH and SISH may be used for many of the same applications as FISH, and have the additional advantage of allowing for analysis of the underlying tissue morphology, for example in histopathology applications. If FISH is performed, the hybridization mixture may contain sets of distinct and balanced pairs of probes, as described in U.S. Pat. No. 6,730,474, the disclosure of which is incorporated herein by reference in its entirety. For CISH, the hybridization mixture may contain at least one set of probes configured for detection with one or more conventional organic chromogens, and for SISH, the hybridization mixture may contain at least one set of probes configured for detection with silver particles, as described in Powell R D et al., "Metallographic in situ hybridization," Hum. Pathol., 38:1145-59 (2007), the disclosure of which is incorporated herein by reference in its entirety.

The present hybridization buffers may also be used fully or partly in all types of molecular biology techniques involving hybridization, including blotting and probing (e.g., Southern, northern, etc.) and arrays.

The method of the present disclosure involves the use of hybridization buffers comprising a sulfone solvent and PVSA or a salt thereof in hybridization of nucleic acid molecules or sequences. The hybridization buffers of the present disclosure are particularly useful in said method.

Hybridization methods using the present hybridization buffers may involve applying the hybridization buffers and at least one nucleic acid probe to a sample comprising a target nucleic acid sequence, most likely in a double stranded form. Usually, in order to secure access for a probe to hybridize with the target sequence, the sample and a hybridization composition comprising the hybridization buffer and at least one nucleic acid probe are mixed and heated to denature the target nucleic acids. During denaturation sulfone solvent interacts with the target sequence and facilitates the denaturation of the target sequence and the re-annealing of the probe to a strand of the target. The sulfone solvents specified in the present disclosure speed up this process considerably and reduce the harshness and toxicity of the hybridization.

Hybridizations using the present hybridization buffers may be performed using the same assay methodology as for hybridizations performed with traditional hybridization buffers. However, the present hybridization buffers allow for shorter hybridization times. For example, the heat pre-treatment, digestion, denaturation, hybridization, washing, and mounting steps may use the same conditions in terms of volumes, temperatures, reagents and incubation times as for traditional compositions. A great variation exists in the traditional hybridization protocols known in the art. For example, some protocols specify a separate denaturation step of potential double stranded nucleotides without probe present, before the following hybridization step. The present hybridization buffers may be used in any of traditional hybridization protocols known in the art.

Alternatively, hybridization assays using the present hybridization buffers can be changed and optimized from traditional methodologies, for example, by decreasing the hybridization time, increasing or decreasing the denaturation and/or hybridization temperatures, and/or increasing or decreasing the hybridization volumes.

According to yet another aspect of the present disclosure, the hybridization energy is provided by heating the hybridization compositions comprising the hybridization buffers and at least one nucleic acid probe. Thus, the step of hybridizing may include the steps of heating and cooling the hybridization composition.

In some embodiments, the denaturation and hybridization steps may occur separately. For example, the specimen may be denatured with a solution without probe and thereafter hybridized with probe.

A further aspect of the present disclosure comprises a method wherein the process of providing a sufficient amount of energy to hybridize the nucleic acids involves a heating process performed by the use of microwaves, hot baths, hot plates, heat wire, peltier element, induction heating, or heat lamps.

According to another aspect the present disclosure provides a method comprising a hybridization protocol, wherein the hybridization protocol is performed in less than about 4 hours, alternatively less than about 3 hours, alternatively less than about 2 hours, alternatively less than about 1 hour.

For example, in some embodiments, the present hybridization buffers will produce strong signals when the denaturation temperature is from about 60° C. to about 95° C. or any temperature between these endpoints and the hybridization temperature is from about 20° C. to about 60° C. or any temperature between these endpoints. In other embodiments, the present hybridization buffers will produce strong signals when the denaturation temperature is from about 60° C. to about 70° C., or about 70° C. to about 80° C., or about 80° C. to about 90° C., or about 90° C. to about 95° C. or any temperature between any of these endpoints, and the hybridization temperature is from about 20° C. to about 30° C., or about 30° C. to about 40° C., or about 40° C. to about 50° C., or about 50° C. to about 55° C., or about 55° C. to about 60° C. or any temperature between any of these endpoints. In other embodiments, the present hybridization buffers will produce strong signals when the denaturation temperature is about 72° C., about 82° C., or about 92° C., and the hybridization temperature is about 37° C., about 40° C., about 45° C., about 50° C. or about 55° C. In other embodiments, the present hybridization buffers will produce strong signals when the denaturation time is from about 0 minutes to about 10 minutes or any time between these two endpoints and the hybridization time is from about 0 minutes to about 24 hours or any time between these two endpoints. In other embodiments, the present compositions will produce strong signals when the denaturation time is from about 0 minutes to about 5 minutes or any time between these two endpoints and the hybridization time is from about 0 minutes to about 8 hours or any time between these two endpoints. In other embodiments, the present hybridization buffers will produce strong signals when the denaturation time is about 0 minutes, about 1 minute, about 2 minutes, about 3 minutes, about 4 minutes, or about 5 minutes, and the hybridization time is about 0 minutes, about 5 minutes, about 15 minutes, about 30 minutes, about 60 minutes, about 180 minutes, or about 240 minutes. It will be understood by those skilled in the art that in some cases, e.g., RNA detection, a denaturation process is not required.

Accordingly, hybridization processes using the present compositions may be performed in less than 8 hours. In some embodiments, the hybridization process is performed in less than 6 hours. In other embodiments, the hybridization process is performed within about 4 hours, alternatively within about 3 hours, alternatively within about 2 hours, alternatively within about 1 hour, alternatively within about 30 minutes, alternatively within about 15 minutes, alternatively within about 10 minutes, alternatively within about 5 minutes. As hybridization time changes, the concentration of probe may also be varied in order to produce strong signals and/or reduce background. For example, as hybridization time decreases, the amount of probe may be increased in order to improve signal intensity. On the other hand, as hybridization time decreases, the amount of probe may be decreased in order to improve background staining.

In some embodiments, the present methods and hybridization buffers are substantially free of a blocking process or blocking agent during hybridization. In traditional hybridization protocols, a blocking process is employed for improving signal and background intensity by blocking the binding of, e.g., repetitive sequences to the target DNA. In the present methods and hybridization buffers, there may be no need to use total human DNA, blocking-PNA, COT-1 DNA, or DNA from any other source as a blocking agent.

However, background levels can be further reduced by adding agents that reduce non-specific binding, such as to the cell membrane, such as small amounts of total human DNA or non-human-origin DNA (e.g., salmon sperm DNA) to a hybridization reaction using the present hybridization buffers.

The present hybridization buffers furthermore provide for the possibility to considerably reduce the concentration of probe nucleic acid sequences used in the hybridization process. Generally, the concentration of probes may be reduced from 2 to 8-fold compared to traditional concentrations. For example, if HER2 DNA probes and CEN17 PNA probes are used with the present hybridization buffers, their concentrations may be reduced compared to their concentrations with traditional hybridization buffers. This feature, along with the absence of any requirement for blocking DNA, such as blocking-PNA or COT1, allows for an increased probe volume in automated instrument systems compared to the traditional 10 µL, or less, volume used in traditional manual systems, which reduces loss due to evaporation, as discussed in more detail below.

Reducing probe concentration also reduces background. However, reducing the probe concentration is inversely related to the hybridization time, i.e., the lower the concentration, the higher hybridization time required. Nevertheless, even when extremely low concentrations of probe are used with the present hybridization buffers, the hybridization time is still shorter than with traditional hybridization buffers.

The present hybridization buffers often allow for better signal-to-noise ratios than traditional hybridization buffers. For example, with certain probes, a one hour hybridization with the present hybridization buffers will produce similar background and stronger signals than an overnight hybridization in a traditional hybridization buffer.

Traditional hybridization assay methods may also be changed and optimized when using the present hybridization buffers depending on whether the system is manual, semi-automated, or automated. For example, a semi- or an automated system will benefit from the short hybridization times and the reduced need for mixing with the present hybridization buffers. The short hybridization time may reduce the difficulties encountered when traditional hybridization buffers are used in such systems. For example, one problem with semi- and automated systems is that significant evaporation of the sample can occur during hybridization, since such systems require small sample volumes (e.g., 10-150 µL), elevated temperatures, and extended hybridization times (e.g., 14 hours). Thus, proportions of the components in traditional hybridization buffers are fairly invariable. However, since the present hybridization buffers allow for faster hybridizations, evaporation is reduced, allowing for increased flexibility in the proportions of the components in hybridization buffers used in semi- and automated systems.

The disclosure may be understood more clearly with the aid of the non-limiting examples that follow, which constitute preferred embodiments of the compositions according to the disclosure. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

Any ranges described herein are understood to include all numbers in between the endpoints of the range.

All references cited herein are incorporated by reference herein in their entireties.

The examples that follow illustrate the present disclosure and should not in any way be considered as limiting the invention.

EXAMPLES

Example 1

A hybridization buffer according to the present disclosure was tested in a FISH staining procedure. The components of the hybridization buffer are shown in Table 2.

TABLE 2

| Component | Concentration |
|---|---|
| Sulfolane | 13% (v/v) |
| Dextran sulfate, highly sulfated (MW 500,000) | 10% (w/v) |
| Poly vinyl sulfonic acid (Na-salt) (MW 3,000-10,000) | 30% (w/v) |
| NaCl | 900 mM |
| MOPS buffer pH 7.2 | 40 mM |

Example 2

In this example, the hybridization buffer of Example 1 was combined with probes and tested in hybridization assays. The hybridization buffers were combined with probes available from Agilent Technologies that were dilutions of the DNA based sureFISH RET break apart (BA) probe having CY3/FITC labels or the DNA/PNA based enumeration probe HER2/CEN-17 having Texas Red/FITC labels to form hybridization compositions. These hybridization compositions were used to perform FISH staining on slides with FFPE human tissues. The slides contained tonsil tissues, breast carcinoma tissue, kidney tissue and colon tissue. The samples were treated with the hybridization composition in accordance with a standard histology protocol, except that a relatively high denaturation temperature (80° C. as opposed to 66° C.) was used to suit the present hybridization composition. Specifically, the histology protocol was carried out as follows:

1. Deparaffinization in xylene and alcohols
2. Rehydration in alcohols
3. Heat pretreatment in a microwave for 10 min in pretreatment buffer
4. Pepsin treatment with pepsin by immersion at 37° C.
5. Dehydration in alcohols
6. Application of the hybridization buffer containing probe to the tissue
7. Denaturation at 80° C. for 10 min
8. Hybridization at 45° C. for 2 hours
9. Stringent wash at 63° C. in stringent wash buffer for 10 min 10. Dehydration in alcohols
11. Mounting in fluorescence mounting medium
12. Fluorescence microscopy and evaluation of staining quality Following completion of the FISH staining procedure, the samples were analyzed to ascertain staining quality by the hybridization composition using fluorescence microscopy with relevant filters for Texas Red, CY3 and FITC. Staining results (signal quality) were given a score from 0 to 3 where a score of 0 indicates no signal and a score of 3 indicates maximum signal. A score of 2 or higher indicates an acceptable staining result. Scores may be given in halves and quarters. Staining scores on FFPE tissue using the hybridization buffer of Table 2 are provided in Table 3 below. Probe concentrations are given relative to a commercially relevant concentration of 1x.

TABLE 3

| Hybridization buffer | Probe | Probe concentration (relative) | FISH signal scores Red | Green |
|---|---|---|---|---|
| Example 1 | HER2/CEN-17 | 0.125x | 2.5 | 2.5 |
| Example 1 | HER2/CEN-17 | 0.125x | 2.5 | 2.5 |
| Example 1 | HER2/CEN-17 | 0.25x | 3 | 2.5 |
| Example 1 | HER2/CEN-17 | 0.25x | 2.75 | 2.5 |
| Example 1 | sureFISH RET | 0.125x | 3 | 2.25 |
| Example 1 | sureFISH RET | 0.125x | 2.5 | 2.25 |
| Example 1 | sureFISH RET | 0.25x | 2.5 | 2.5 |
| Example 1 | sureFISH RET | 0.25x | 2.5 | 2.5 |

These results demonstrate that the tested hybridization composition with a low probe concentration relative to a commercial relevant probe concentration provides high quality FISH staining of FFPE tissue samples when stained as described above.

Example 3

The stability of a hybridization buffer of the present disclosure compared to an existing hybridization buffer comprising ethylene carbonate was analyzed in an accelerated stability test. The hybridization buffer of the present disclosure (test) and the hybridization buffer that was included as a comparative control had the following components:

TABLE 4

| Component | Existing buffer | Hybridization buffer (test) |
|---|---|---|
| Sulfolane | — | 13% (v/v) |
| Ethylene carbonate | 15% (v/v) | — |
| DS500 | 20% (w/v) | 10% (w/v) |
| PVSA sodium salt | NA | 14% (w/v) |
| NaCl | 600 mM | 200 mM |
| Citrate buffer pH 6.2 | 10 mM | 10 mM |

To accelerate stability testing, probe mixes based on the hybridization buffers in Table 4 were stored at 2-8° C., 22° C. and 37° C. The temperature of 2-8° C. reflects desired storage and the temperatures of 22° C. and 37° C. reflect accelerated storage, as one day at a higher temperature reflects a greater number of days at the desired storage as calculated using models based on the Q-rule and the Arrhenius equation with a conservative Q10 of 1.8 Hybridization compositions containing probe mixed with the test hybridization buffer of the present disclosure and the comparative control hybridization buffer were prepared so that the results could be compared. Hybridization compositions containing probe mixed with the test hybridization buffers were prepared and transferred to the various storage conditions as described below. On the next day, time point zero (T0) FISH performance data is generated. 250 µL volume screw cap PE tubes were used in this stability experiment to reduce the air volume above the probe mix. Probe mixes were named according to the table below and stored at the designated locations. Mixing of the existing buffer prior to any test was done by pipette mixing. The buffers of the present disclosure were not mixed in order to give worst case conditions for homogeneity and stability. In addition, pipetting from these test samples was done from the top part of the liquid volume when a sample was drawn for FISH performance testing.

The details for the calculated accelerated storage times are as follows (Tables 5 and 6):

TABLE 5

Calculated storage acceleration

| Desired storage temp (° C.) | 5 | | | |
|---|---|---|---|---|
| Accelerated temp. (° C.) | 37 | | | |
| Temp increase (° C.) | 32 | | | |
| days per month | 30.4 | | | |
| acceleration factor | 6.559519 | | | |
| Days accelerated | 0 | 37 | 65 | 105 |
| RTE = equivalent days at desired storage temp | 0.0 | 279.4 | 491.4 | 793.7 |
| Corresponds to months of desired storage | 0.0 | 9.2 | 16.2 | 26.1 |

TABLE 6

Calculated storage acceleration

| Desired storage temp (° C.) | 5 | | | |
|---|---|---|---|---|
| Accelerated temp. (° C.) | 22 | | | |
| Temp increase (° C.) | 17 | | | |
| days per month | 30.4 | | | |
| acceleration factor | 2.716209 | | | |
| Days accelerated | 0 | 37 | 65 | 105 |
| RTE = equivalent days at desired storage temp | 0.0 | 137.5 | 241.6 | 390.2 |
| Corresponds to months of desired storage | 0.0 | 4.5 | 7.9 | 12.8 |

A FFPE tissue block was used in this study. Red and green signal intensity on the FFPE tissue was analyzed following FISH tests performed at the following times (T0, T1, T2 and T3) as shown below (Table 7):

TABLE 7

| | T0 | T1 | T2 | T3 |
|---|---|---|---|---|
| Days (real time) | 0 | 37 | 65 | 105 |
| Fridge 2-8° C. (= real time) RTE days/months | 0 days | 37 days = 1.2 months | 65 days = 2.1 months | 105 days = 3.5 months |
| At 22° C. RTE days/months | 0 days | 138 days = 4.5 months | 242 days = 7.9 months | 390 days = 12.8 months |
| At 37° C. RTE days/months | 0 days | 279 days = 9.2 months | 491 days = 16.2 months | 794 days = 26.1 months |

RTE = real time equivalents

The FISH protocol included pepsin immersion at 37° C. for 30 min, denaturation 80° C. 10 min and hybridization 45° C. for 120 min.

Tissue was scored in accordance with standard scoring procedures, scaled 0 to 3, for Texas Red and FITC signals from the HER2/CEN-17 probe or from CY3 and FITC signals from the sureFISH RET BA probe. To monitor impact of possible inhomogeneity, the vials containing the hybridization buffer of the present disclosure (test) were not mixed prior to testing. The comparative control buffer included as a control was mixed in accordance with manufacturer's instructions. Scoring was performed by two different observers and were performed blinded and results unblinded after scoring was complete.

The initial FISH test was performed at T0 (Table 8) on each batch of probe mix before stability storage. Results at T0 are as follows:

TABLE 8

| Slide # | Hybridization buffer and probe | Time (days) | Equivalent days of storage at 2-8° C. | Observer 1 | | Observer 2 | |
|---|---|---|---|---|---|---|---|
| | | | | Red | Green | Red | Green |
| 1A | # A (comparative control) HER2/CEN-17 | 0 | NA | 2.75 | 2.5 | 2.75 | 2.5 |
| 1B | # B (comparative control) SureFISH RET BA | 0 | NA | 2.5 | 2.25 | 2.75 | 2.5 |
| 2A | # A (comparative control) HER2/CEN-17 | 0 | NA | 3 | 2.5 | 3 | 2.5 |
| 2B | # B (comparative control) SureFISH RET BA | 0 | NA | 3 | 2.75 | 3 | 3 |
| 3A | # C (test) HER2/CEN-17 | 0 | NA | 3 | 2.75 | 3 | 3 |
| 3B | # D (test) SureFISH RET BA | 0 | NA | 2.25 | 2.25 | 2.5 | 2.5 |
| 4A | # C (test) HER2/CEN-17 | 0 | NA | 3 | 2.5 | 3 | 2.5 |
| 4B | # D (test) SureFISH RET BA | 0 | NA | 3 | 2.75 | 3 | 2.75 |

The second FISH test was performed at T1 (Table 9) on each batch of probe mix. Results at T1 are as follows:

TABLE 9

| Slide # | Vial name | Hybridization buffer and probe | Equivalent months of storage at 2-8° C. | Observer 1 | | Observer 2 | |
|---|---|---|---|---|---|---|---|
| | | | | Red | Green | Red | Green |
| 1A | # A_fridge | Comparative | 1.2 | 2.5 | 2.5 | 2.75 | 3 |
| 1B | # A_RT | control | 4.5 | 2.75 | 2.5 | 2.75 | 2.75 |
| 2A | # A_37 | HER2/CEN-17 | 9.2 | 1.5 | 2.5 | 1.75 | 3 |
| 2B | # A_freeze | | NA | 3 | 2.5 | 2.75 | 2.75 |
| 3A | # B_fridge | Comparative | 1.2 | 2.25 | 2 | 2.25 | 2.25 |
| 3B | # B_RT | control RET | 4.5 | 2 | 2 | 2.25 | 2.25 |
| 4A | # B_37 | BA | 9.2 | 2 | 1 | 2 | 1.5 |
| 4B | # B_Freeze | | NA | 2.75 | 2 | 2.75 | 2.5 |
| 5A | # C_fridge | Test | 1.2 | 2.25 | 2.5 | 2.25 | 2.75 |
| 5B | # C_RT | HER2/CEN-17 | 4.5 | 2.5 | 2.5 | 2.5 | 2.5 |
| 6A | # C_37 | | 9.2 | 2.5 | 2.5 | 3 | 2.75 |
| 7A | # D_fridge | Test | 1.2 | 2.75 | 2 | 2.75 | 2.25 |
| 7B | # D_RT | RET BA | 4.5 | 2.75 | 2 | 2.75 | 2.25 |
| 8A | # D_37 | | 9.2 | 3 | 2.5 | 3 | 2.5 |

All vials were equilibrated to room temperature before use. All # A, B vials were mixed (tip mix) prior to probe application, while remaining vials were not. This is done to include worst case scenario of both instability and inhomogeneity for vials C and D. Red indicates the red signal score, Green indicates the green signal score.

The third FISH test was performed at T2 on each batch of probe mix before stability storage. Results at T2 (Table 10) are as follows:

TABLE 10

| Slide # | Vial name | Hybridization buffer and probe | Equivalent months of storage at 2-8° C. | Observer 1 Red | Observer 1 Green | Observer 2 Red | Observer 2 Green |
|---|---|---|---|---|---|---|---|
| 1A | #A_fridge | Comparative control | 2.1 | 3 | 2.5 | 3 | 3 |
| 1B | #A_RT | | 7.9 | 2.75 | 2.5 | 2.75 | 2.75 |
| 2A | #A_37 | HER2/CEN-17 | 16.2 | 1 | 2.5 | 1 | 2.25 |
| 2B | #A_freeze | | NA | 3 | 2.5 | 3 | 2.5 |
| 3A | #B_fridge | Comparative control | 2.1 | 3 | 2.5 | 2.75 | 2.75 |
| 3B | #B_RT | RET BA | 7.9 | 2-2.5 | 2-2.5 | 2.5 | 2.25 |
| 4A | #B_37 | | 16.2 | 2 | 1 | 2 | 1.5 |
| 4B | #B_Freeze | | NA | 2-3 | 2.5 | 2.75 | 2.5 |
| 5A | #C_fridge | Test | 2.1 | 3 | 2.5 | 3 | 2.75 |
| 5B | #C_RT | HER2/CEN-17 | 7.9 | 2.5 | 2.5 | 2.75 | 2.75 |
| 6A | #C_37 | | 16.2 | 3 | 2.5 | 3 | 2.5 |
| 7A | #D_fridge | Test | 2.1 | 3 | 2.25 | 3 | 2 |
| 7B | #D_RT | RET BA | 7.9 | 2.5 | 2.25-2.5 | 2.75 | 2.5 |
| 8A | #D_37 | | 16.2 | 3 | 2.5 | 3 | 2.75 |

The fourth FISH test was performed at T3 (Table 11) on each batch of probe mix before stability storage. Results at T3 are as follows:

TABLE 11

| Slide # | Vial name | Hybridization buffer | Equivalent months of storage at 2-8° C. | Observer 1 Red | Observer 1 Green | Observer 2 Red | Observer 2 Green |
|---|---|---|---|---|---|---|---|
| 1A | #A_fridge | Comparative control | 3.5 | 2.75 | 2.5 | 2.75 | 2.75 |
| 1B | #A_RT | | 12.8 | 2.5 | 2.5 | 2.25 | 2.5 |
| 2A | #A_37 | HER2/CEN-17 | 26.1 | 0.5 | 2.25 | 0.5 | 2.5 |
| 2B | #A_freeze | | NA | 3 | 2.5 | 3 | 3 |
| 3A | #B_fridge | Comparative control | 3.5 | 3 | 2.5 | 2.75 | 2.75 |
| 3B | #B_RT | | 12.8 | 2.5 | 2 | 2.25 | 2 |
| 4A | #B_37 | RET BA | 26.1 | 2 | 1 | 2 | 1.5 |
| 4B | #B_Freeze | | NA | 2.5 | 2.25 | 2.25 | 2 |
| 5A | #C_fridge | Test | 3.5 | 2.5 | 2.5 | 2.5 | 2.75 |
| 5B | #C_RT | HER2/CEN-17 | 12.8 | 2.5 | 2.25 | 3 | 2.75 |
| 6A | #C_37 | | 26.1 | 2.25 | 2 | 2.25 | 2.5 |
| 7A | #D_fridge | Test | 3.5 | 3 | 2.25 | 3 | 2.25 |
| 7B | #D_RT | RET BA | 12.8 | 2.5 | 2 | 3 | 2.25 |
| 8A | #D_37 | | 26.1 | 3 | 2.5 | 3 | 2.5 |

All vials were equilibrated to room temperature before use. All # A and # B vials were mixed prior to probe application, while remaining vials were not. This is done to include worst case scenario of both instability and inhomogeneity for vials B, C and D.

Figure 1B:
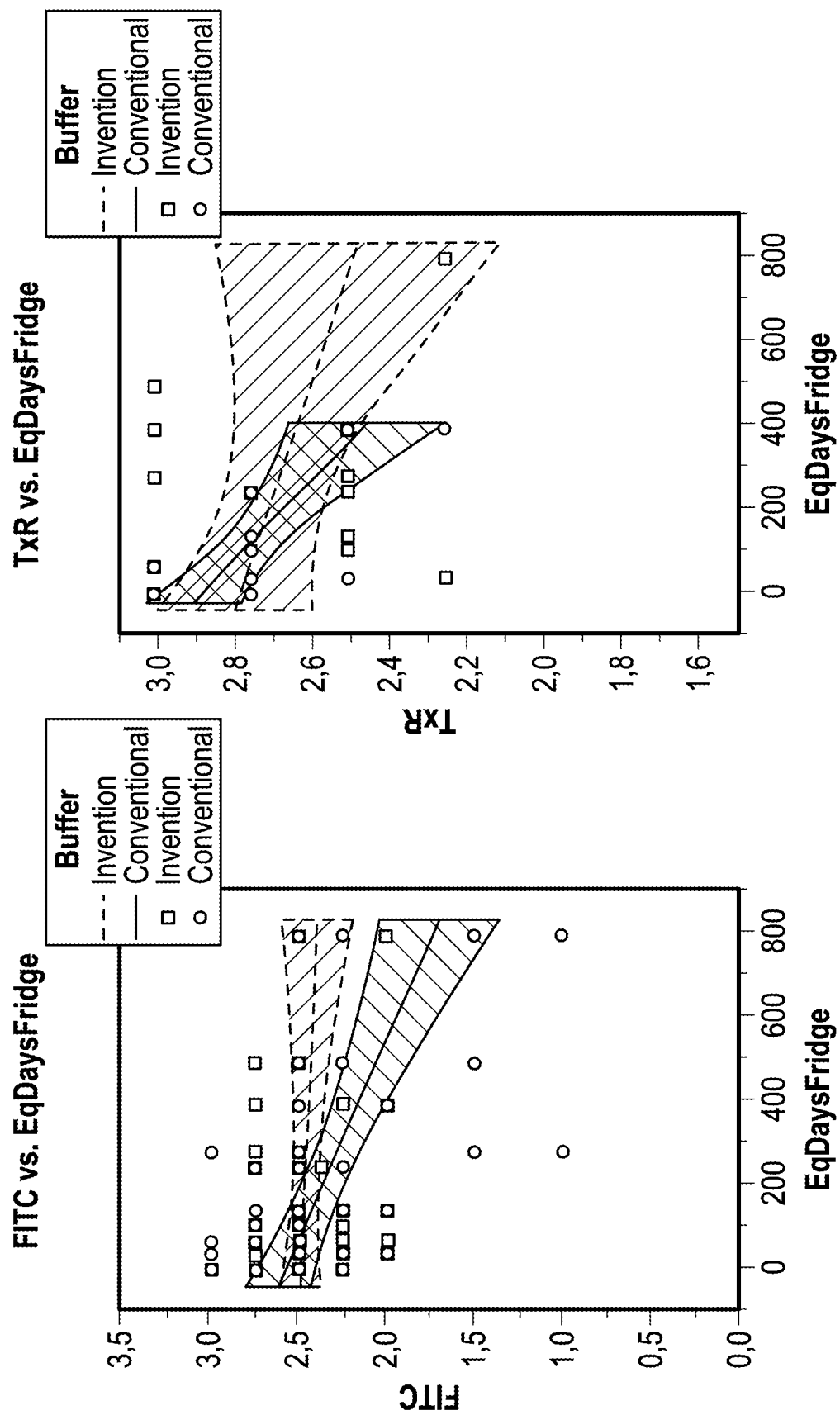
Figure 1C:
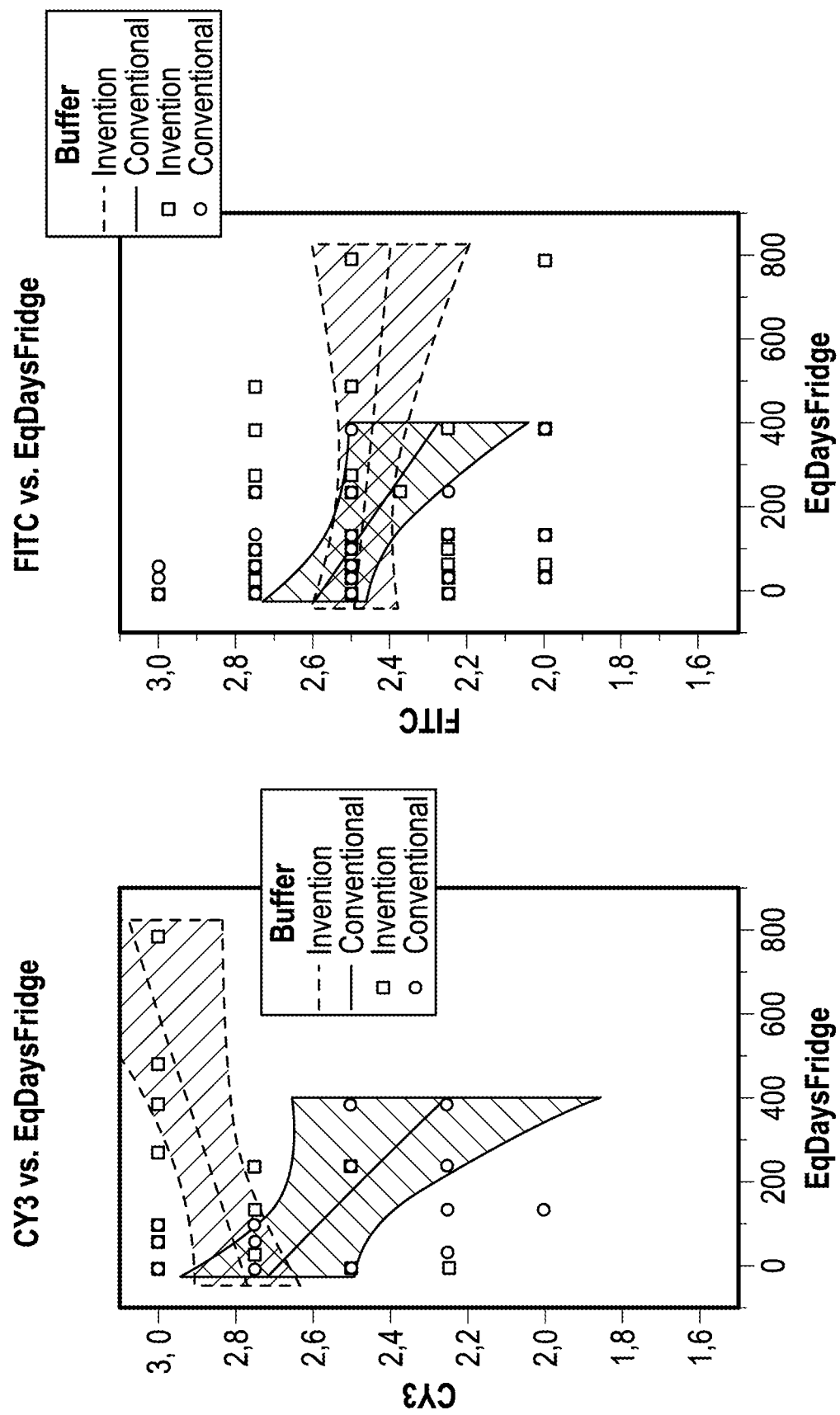

Analysis of the data gathered from the accelerated stability test is presented in FIG. 1 and demonstrates that the hybridization buffers of the present disclosure can withstand storage much better than the comparative control hybridization buffers, even at a temperature as high as 37° C. In FIG. 1, the x axis defines the equivalent days at 5° C. from acceleration start and the y axis is the functional FISH staining intensity for the different labels. These data show that hybridization buffers comprising sulfolane and PVSA sodium salt have better stability than a comparative control buffer since the slopes of the sulfolane/PVSA sodium salt buffer are smaller.

Table 12 provides average data (Observer 1/Observer 2 average) in a transposed manner to demonstrate changes at different storage conditions when the buffer of the present disclosure (test) is compared to a comparative control buffer.

TABLE 12

| | A) HER2/CEN-17 Comparative control | | C) HER2/CEN17 Test | | B) RET BA Comparative control | | D) RET BA Test | |
|---|---|---|---|---|---|---|---|---|
| | Red | Green | Red | Green | Red | Green | Red | Green |
| Day 0 | 2.9 | 2.5 | 3 | 2.7 | 2.8 | 2.6 | 2.7 | 2.6 |
| Day 37, fridge | 2.6 | 2.75 | 2.25 | 2.6 | 2.25 | 2.1 | 2.75 | 2.1 |
| Day 65, fridge | 3 | 2.75 | 3 | 2.6 | 2.8 | 2.6 | 3 | 2.1 |
| Day 105, fridge | 2.75 | 2.6 | 2.5 | 2.6 | 2.9 | 2.6 | 3 | 2.25 |
| Day 37, RT | 2.75 | 2.6 | 2.5 | 2.5 | 2.1 | 2.1 | 2.75 | 2.1 |
| Day 65, RT | 2.75 | 2.6 | 2.6 | 2.6 | 2.1 | 2.25 | 2.6 | 2.3 |
| Day 105, RT | 2.4 | 2.5 | 2.75 | 2.5 | 2.4 | 2 | 3 | 2.1 |
| Day 37, 37° C. | 1.6 | 2.75 | 2.75 | 2.6 | 2 | 1.25 | 3 | 2.5 |
| Day 65, 37° C. | 1 | 2.4 | 3 | 2.5 | 2 | 1.5 | 3 | 2.6 |
| Day 105, 37° C. | 0.5 | 2.4 | 2.25 | 2.25 | 2 | 1.25 | 3 | 2.5 |
| Day 37, freeze | 2.8 | 2.6 | NA | NA | 2.75 | 2.25 | NA | NA |
| Day 65, freeze | 3 | 2.5 | NA | NA | 2.6 | 2.5 | NA | NA |
| Day 105, freeze | 3 | 2.75 | NA | NA | 2.4 | 2.1 | NA | NA |

In conclusion, the accelerated stability data indicate very good stability of sureFISH RET BA or HER2/CEN-17 probe mixes prepared with hybridization buffers of the present disclosure, such as buffers containing sulfolane and PVSA sodium salt. The present hybridization buffer is more stable compared to comparative control hybridization buffers and is more convenient to use since mixing is not required.

Also, since samples from the probe mixes containing the hybridization buffer of the present disclosure were taken from the tube top without mixing at any time during the tests, these data also indicate that once probe mixes are mixed to homogeneity, they stay homogeneous irrespective of storage temperature (5° C., 22° C. and 37° C.). However, for the comparative control hybridization buffer, tip-mixing was performed with a pipette on samples before use. The data generated therefore, represents a worst case scenario for the hybridization buffers of the present disclosure, and even in this scenario, the present buffers still outperformed the comparative control buffers. Finally, the SAS-JMP software based degradation/stability model predicts a minimum of 34 months stability at 5° C. for hybridization buffers of the present disclosure.

Example 3

Hybridization buffers of the present disclosure were tested for evaporation and robustness in capillary fields, and for performance in FISH assays. In this example, hybridization buffers of the present disclosure were prepared with 13%, 14.3% and 14.9% (v/v) sulfolane and compared to see how the solvent concentration affects robustness towards water loss/phase separation and FISH performance.

The different hybridization buffers of the present disclosure that were tested are designated Test 1, 2 and 3 to indicate the different sulfolane solvent concentrations that were tested (Table 13). The hybridization buffers were prepared in 5 mL volumes using high precision volumetric flasks and comprised the following components:

TABLE 13

| Hybridization buffer | Sulfolane (%, v/v) | Dextran Sulfate (%, w/v) | PVSA sodium salt (%, w/v) | NaCl (mM) | MOPS (mM) |
|---|---|---|---|---|---|
| Test 1 | 13 | 10 | 30 | 900 | 40 |
| Test 2 | 14.3 | 10 | 30 | 900 | 40 |
| Test 3 | 14.9 | 10 | 30 | 900 | 40 |

The homogeneity of the hybridization buffers was determined by using the blue dye erioglaucine to facilitate visual monitoring. 1 mL samples of the homogenized hybridization buffers were added to tubes with screw lid (2 mL Sarstedt tube) and mixed to homogeneity with 4 µL of a 5% (w/v) erioglaucine solution that was added to each tube. Samples with erioglaucine were then centrifuged for 1 h at 5000×g in an Ole Dich centrifuge at 2° C. or at 15° C. Following each centrifugation, the hybridization buffer samples were visually evaluated for homogeneity and phase separation. The results, provided in Table 14 below, demonstrate that the hybridization buffers of the present disclosure are homogeneous and maintain homogeneity under the tested conditions.

TABLE 14

| Hybridization buffer | Sulfolane (%, v/v) | Solubility (appearance) RT (mix o/n) | Solubility (appearance) 15° C. | Solubility (appearance) 2° C. |
|---|---|---|---|---|
| Test 1 | 13 | Clear | Clear | Clear |
| Test 2 | 14.3 | Clear | Clear | Clear |
| Test 3 | 14.9 | Clear | Clear | Clear |

Next, the prepared hybridization buffers were tested for their robustness towards inhomogeneity during a simulated denaturation and hybridization test in a hybridizer setup with spacers in the corners of the slide/coverslip to generate the capillary field. Phase separation during denaturation and hybridization will change the distribution of the blue dye into a dark blue phase and a clearer phase and the homogeneous area can be quantified from the image.

To perform these tests, Flex slides were used as bottom slide and Flex slide glass cut to the required staining area (25×45 mm) was used as the top slide. Kaplon tape was added to the four corners of the 25×45 mm flex glass to define the capillary gap size. With double Kaplon layers the resulting capillary field has a calculated volume of 25 mm×45 mm×0.1 mm=112.5 mm$^3$ or µL. 125 µL of hybridization buffer is routinely used to fill this capillary field.

Simulation of denaturation for 10 min at 80° C. and hybridization for 120 min at 45° C. was performed on a hybridizer with two wetted humidity strips as is used during standard manual FISH staining procedures. Images of reagent spreading before and after the simulation were taken to calculate the percent homogeneous buffer area.

The results from the hybridization simulation, summarized in the table below, demonstrate that the hybridization buffers of the present disclosure are homogeneous and maintain acceptable homogeneity in a capillary field during denaturation and hybridization steps of a FISH procedure (Table 15).

TABLE 15

| Hybridization buffer | Sulfolane (v/v, %) | NaCl (mM) | % average homogeneous staining area |
|---|---|---|---|
| Test 1 | 13 | 900 | 71 |
| Test 2 | 14.3 | 900 | 60 |
| Test 3 | 14.9 | 900 | 52 |

Example 4

Hybridization buffers of the present disclosure with various NaCl concentrations were tested for performance in capillary field experiments. These exemplary hybridization buffers of the present disclosure have relatively high NaCl concentrations (e.g., 13.1% (v/v) sulfolane, 30% (w/v) PVSA sodium salt, 10% (v/v) DS500, 40 mM MOPS pH 7.2, and 900 mM NaCl). Without wishing to be bound by theory, high NaCl concentration is believed to reduce evaporation in the capillary field. In this example, four different NaCl concentrations were tested to investigate the magnitude of the effect and the effect on functional performance.

2.5 mL of the following four exemplary hybridization buffers (Table 16) of the present disclosure were produced and tested. One mL of each homogenized hybridization buffer was added into a screw top tube (1 mL Sarstedt tube) with blue dye. The blue dye erioglaucine (4 µL of a 5% (w/v) erioglaucine per mL of hybridization buffer) was used to facilitate visual monitoring of phase separation. All four buffers were homogeneous, clear solutions with no phase separation observed at room temperature or at 15° C. and 2° C. following the homogeneity test by centrifugation described above.

TABLE 16

| Hybridization buffer | Sulfolane (%, v/v) | Dextran Sulfate (%, w/v) | PVSA sodium salt (%, w/v) | NaCl (mM) | MOPS buffer pH 7.2 (mM) |
|---|---|---|---|---|---|
| 1 | 13.1 | 10 | 30 | 900 | 40 |
| 2 | 13.1 | 10 | 30 | 700 | 40 |
| 3 | 13.1 | 10 | 30 | 500 | 40 |
| 4 | 13.1 | 10 | 30 | 300 | 40 |

The four exemplary hybridization buffers of the present disclosure, containing various NaCl concentrations, were then tested for robustness in a capillary field The hybridization buffers were tested as described below for their robustness towards inhomogeneity during a simulated denaturation and hybridization test in a hybridizer setup with spacers in the corners of the slide/coverslip to generate the capillary field. Phase separation during denaturation and hybridization is observed as a change in the distribution of the erioglaucine dye into a dark blue phase and a clearer phase. The homogeneous area was then quantified from images of the stained buffers.

To perform these tests, Flex slides are used as the bottom slide and Flex slide glass cut to the required staining area (25×45 mm) was used as the top layer. Kaplon tape was added to the four corners of the 25×45 mm Flex glass to define the capillary gap size. With double Kaplon tape layers, the resulting capillary field has a calculated volume of 25 mm×45 mm×0.1 mm=112.5 mm$^3$ or µL. 1254, of hybridization buffer is routinely used to fill this capillary field.

Simulation of denaturation for 10 min at 80° C. and hybridization for 120 min at 45° C. was performed on hybridizer with two wetted humidity strips as used during standard FISH staining procedures. Images of reagent spreading before and after the simulation were taken to calculate the percent homogeneous buffer area.

The calculated areas are based on standard determination of the homogeneous area and the results are summarized as follows (Table 17):

TABLE 17

| Hybridization buffer | % average homogeneous staining area |
|---|---|
| 1 | (62 + 63)/2 = 62.5 |
| 2 | (59 + 56)/2 = 57.5 |
| 3 | (51 + 57)/2 = 54 |
| 4 | (52 + 50)/2 = 51 |

The hybridization buffers of the present disclosure containing various NaCl concentrations were then analyzed for performance in FISH staining procedures (Table 18). The FISH staining tests were performed with HER2/CEN-17 probes at a relative concentration to a commercial relevant probe concentration of 0.125× and 0.25× in the different hybridization buffers on FFPE tissue. A comparative control buffer containing 15% (v/v) ethylene carbonate, 20% (w/v) dextran sulfate, 600 mM NaCl and 10 mM Citrate buffer pH 6.2 was also included for reference and as a control.

The FISH staining procedure included pepsin immersion at 37° C. for 30 min, denaturation at 80° C. for 10 min and hybridization at 45° C. for 120 min.

Scoring was performed blinded for the observers with respect to the buffer used on a fluorescence microscope with appropriate filters for Texas Red and FITC. Tissue was scored in accordance with standard scoring procedures, scaled 0 to 3, with 0 indicating no signal, 3 indicating maximum signal and 2 indicating an acceptable positive signal. Results from the FISH staining are as follows:

TABLE 18

| Slide no | Hybridization Buffer | HER2/CEN-17 conc. | FISH signal score Red | FISH signal score Green |
|---|---|---|---|---|
| 1A | 1 | 0.25 | 2.5 | 2.5 |
| 1B | 1 | 0.125 | 2.25 | 2.25 |
| 2A | Comparative control | 0.25 | 2.5 | 2.25 |
| 2B | Comparative control | 0.125 | 2.5 | 2.25 |
| 3A | 2 | 0.25 | 2.5 | 2.5 |
| 3B | 2 | 0.125 | 2.5 | 2.5 |
| 4A | 3 | 0.25 | 3 | 2.5 |
| 4B | 3 | 0.125 | 2.5 | 2.5 |
| 5A | 4 | 0.25 | 3 | 2.5 |
| 5B | 4 | 0.125 | 2.5 | 2.5 |
| For slides 6-8 below, the capillary cover was 0.1 mm with 125 µL probe applied | | | | |
| 6A | 1 | 0.25 | 2.25 | 2.25 |
| 6B | 1 | 0.25 | 2.25 | 2.25 |
| 7A | Comparative control | 0.25 | 2.5 | 2.25 |
| 7B | Comparative control | 0.25 | 2.5 | 2.5 |
| 8A | 4 | 0.25 | 2.75 | 2.5 |
| 8B | 4 | 0.25 | 2.5 | 2.5 |

In conclusion, the four tested hybridization buffers with reductions in NaCl concentrations are homogeneous when prepared and following the homogeneity tests at 0 and 15° C. The tested hybridization buffers of the present disclosure also demonstrated robustness against evaporation in unprotected capillary fields. The altered NaCl concentrations were observed to affect the capillary field performance. Without wishing to be bound by theory, it is believed that altering NaCl concentrations is likely to cause a change in vapor pressure. The average homogeneous staining area is reduced by approximately 18% (nominal 11.5%) when reducing NaCl from 900 mM to 300 mM.

With respect to the FISH staining performance, the data show that a reduction in NaCl from 900 mM to 300 mM marginally increases red signal score with 0.25 to 0.5 depending on the probe concentration.

Example 5

Homogeneity and performance of hybridization buffers of the present disclosure were tested with sulfolane from two different manufacturers in order to determine if the source of the sulfolane would affect buffer performance. In addition, inclusion of low concentration Sodium-Phosphate in hybridization buffers of the present disclosure was investigated. The following hybridization buffers were tested (Table 19):

TABLE 19

| Hybridization buffers | | | | | | | |
|---|---|---|---|---|---|---|---|
| Hybridization buffer | Sulfolane source | Sulfolane (%, v/v) | Dextran Sulfate (%, w/v) | PVSA sodium salt (%, w/v) | NaCl (mM) | Sodium phosphate (mM) | MOPS (mM) |
| 1 | Manufacturer 1 | 13.1 | 10 | 30 | 900 | 0 | 40 |
| 2 | Manufacturer 2 | 13.1 | 10 | 30 | 900 | 0 | 40 |
| 3 | Manufacturer 2 | 14.8 | 10 | 30 | 900 | 0 | 40 |
| 4 | Manufacturer 2 | 15.75 | 10 | 30 | 900 | 0 | 40 |
| 5 | Manufacturer 1 | 13.1 | 10 | 30 | 900 | 10 | 40 |
| 6 | Manufacturer 1 | 13.1 | 10 | 30 | 900 | 40 | 0 |

In order to test for homogeneity, blue dye (erioglaucine at 4 μL of a 5% (w/v) erioglaucine per mL of hybridization buffer) was added to 1 mL of each homogenized hybridization buffer in a tube with screw lid (2 mL Sarstedt tube) to ease visual monitoring of homogeneity. Samples with erioglaucine were then centrifuged for 1 h at 5000×g in an Ole Dich centrifuge at 0° C., 2° C. and at 15° C. Following each centrifugation, samples were visually evaluated for homogeneity and phase separation. The results are as follows (Table 20):

TABLE 20

| Hybridization buffer | Solubility RT (mix o/n) | Solubility 15° C. | Solubility 2° C. | Solubility 0° C. |
|---|---|---|---|---|
| 1 | Clear | Clear | Clear | Clear |
| 2 | Clear | Clear | Clear | Clear |
| 3 | Clear | Clear | Clear | Clear |
| 4 | Clear | Clear | Clear | Clear |
| 5 | Clear | Clear | Clear | Clear |
| 6 | Clear | Clear | Clear | Clear |

The results of the homogeneity testing indicate no difference between sulfolane from Manufacturer 1 or 2 in the performance of the present hybridization buffers.

The hybridization buffers of the present disclosure that were made with sulfolane from different manufacturers were then subjected to FISH staining procedure performance tests. The test was performed with HER2/CEN-17 probes at a relative concentration to a commercial relevant probe concentration of 0.125× and 0.25× in the different hybridization buffers on FFPE breast tissue. An existing buffer containing 15% (v/v) ethylene carbonate, 20% (w/v) dextran sulfate, 600 mM NaCl and 10 mM Citrate buffer pH 6.2 was also included for reference and as a control.

Standard FISH staining procedures including pepsin immersion at 37° C. for 30 min, denaturation at 80° C. for 10 min and hybridization at 45° C. for 120 min. Scoring was performed blinded with no knowledge of the denaturation temperature for each slide on a fluorescence microscope with relevant filters. Scoring utilized standard 0 to 3 range with 0 indicating no signal, 3 indicating maximum signal and 2 indicating acceptable positive signal. The results are presented in the following table (Table 21):

TABLE 21

| Slide no | Hybridization Buffer | HER2/CEN-17 conc. | FISH signal score Red | FISH signal score Green |
|---|---|---|---|---|
| 1A | 1 | 0.2 | 2.5 | 2.75 |
| 1B | 1 | 0.1 | 2 | 2.5 |
| 2A | 2 | 0.2 | 2.5 | 2.5 |
| 2B | 2 | 0.1 | 2.25 | 2.5 |
| 3A | 5 | 0.2 | 3 | 2.75 |
| 3B | 5 | 0.1 | 2.25 | 2.5 |
| 4A | 6 | 0.2 | 2.75 | 2.75 |
| 4B | 6 | 0.1 | 2.25 | 2.5 |
| 5A | Comparative control | 0.25 | 3 | 2.5 |
| 5B | Comparative control | 0.125 | 2.5 | 2.5 |
| 6A | 1 | 0.2 | 2.5 | 2.5 |
| 6B | 1 | 0.1 | 2 | 2.25 |

The results of the FISH performance testing are consistent with the homogeneity data and demonstrate that the sulfolane manufacturer has no effect on the buffers of the present disclosure.

Example 6

Hybridization buffers of the present disclosure were tested at various hybridization temperatures. Since the present hybridization buffers are more stable than certain existing FISH hybridization buffers, it was predicted that they may be able to support a wider range of hybridization temperatures. This example evaluates hybridization temperatures for hybridization buffers of the present disclosure when used in hybridization buffer compositions with HER2/CEN-17 and SureFISH RET BA probes.

The hybridization buffer of the present disclosure that was used in this example contained 13.1% (v/v) sulfolane, 30% (v/v) PVSA sodium salt, 10% (v/v) DS500, 40 mM MOPS pH 7.2, and 900 mM NaCl. The test was performed with both HER2/CEN-17 and RET probe mixes in hybridization buffer at a relative concentration to a commercial relevant probe concentration of 0.125× and 0.25× on FFPE breast tissue. A standard FISH staining protocol was utilized that included pepsin immersion at 37° C. for 30 min and denaturation at 80° C. for 10 min. Hybridization was performed for 120 minutes at test temperatures ranging from 35 to 50° C. as follows (Table 22):

TABLE 22

| ID | Probe | Probe conc. relative | Hybridization temperature (° C.) | Hybridization time (min) |
|---|---|---|---|---|
| 1A | HER2/CEN-17 | 0.25 | 35 | 120 |
| 1B | HER2/CEN-17 | 0.125 | 35 | 120 |
| 2A | HER2/CEN-17 | 0.25 | 38 | 120 |
| 2B | HER2/CEN-17 | 0.125 | 38 | 120 |
| 3A | HER2/CEN-17 | 0.25 | 40 | 120 |
| 3B | HER2/CEN-17 | 0.125 | 40 | 120 |
| 4A | HER2/CEN-17 | 0.25 | 43 | 120 |
| 4B | HER2/CEN-17 | 0.125 | 43 | 120 |
| 5A | HER2/CEN-17 | 0.25 | 45 | 120 |
| 5B | HER2/CEN-17 | 0.125 | 45 | 120 |
| 6A | HER2/CEN-17 | 0.25 | 48 | 120 |
| 6B | HER2/CEN-17 | 0.125 | 48 | 120 |
| 7A | HER2/CEN-17 | 0.25 | 50 | 120 |
| 7B | HER2/CEN-17 | 0.125 | 50 | 120 |
| 8A | RET | 0.25 | 35 | 120 |
| 8B | RET | 0.125 | 35 | 120 |
| 9A | RET | 0.25 | 38 | 120 |
| 9B | RET | 0.125 | 38 | 120 |
| 10A | RET | 0.25 | 40 | 120 |
| 10B | RET | 0.125 | 40 | 120 |
| 11A | RET | 0.25 | 43 | 120 |
| 11B | RET | 0.125 | 43 | 120 |
| 12A | RET | 0.25 | 45 | 120 |
| 12B | RET | 0.125 | 45 | 120 |
| 13A | RET | 0.25 | 48 | 120 |
| 13B | RET | 0.125 | 48 | 120 |
| 14A | RET | 0.25 | 50 | 120 |
| 14B | RET | 0.125 | 50 | 120 |

Scoring was performed blind with respect to the hybridization temperature using a fluorescence microscope with relevant filters. FFPE tissue was scored in accordance with standard scoring procedures, scaled 0 to 3, with 0 indicating no signal, 3 indicating maximum signal and 2 indicating an acceptable positive signal. Results from the FISH staining are as follows:

TABLE 23

| Slide no | Probe | Probe conc. | Hybridization temp. (°C.) | FISH signal score Red | Green |
|---|---|---|---|---|---|
| 1A | HER2/CEN-17 | 0.25 | 35 | 2 | 2.5 |
| 1B | HER2/CEN-17 | 0.125 | 35 | 1.5 | 2.25 |
| 2A | HER2/CEN-17 | 0.25 | 38 | 2.5 | 3 |
| 2B | HER2/CEN-17 | 0.125 | 38 | 2.25 | 2.75 |
| 3A | HER2/CEN-17 | 0.25 | 40 | 2.75 | 2.75 |
| 3B | HER2/CEN-17 | 0.125 | 40 | 2.5 | 2.75 |
| 4A | HER2/CEN-17 | 0.25 | 43 | 2.75 | 2.5 |
| 4B | HER2/CEN-17 | 0.125 | 43 | 2.5 | 2.5 |
| 5A | HER2/CEN-17 | 0.25 | 45 | 3 | 2.5 |
| 5B | HER2/CEN-17 | 0.125 | 45 | 2.5 | 2.5 |
| 6A | HER2/CEN-17 | 0.25 | 48 | 3 | 2.75 |
| 6B | HER2/CEN-17 | 0.125 | 48 | 2.5 | 2.5 |
| 7A | HER2/CEN-17 | 0.25 | 50 | 3 | 2.5 |
| 7B | HER2/CEN-17 | 0.125 | 50 | 2.75 | 2.5 |
| 8A | RET | 0.25 | 35 | 2.25 | 2 |
| 8B | RET | 0.125 | 35 | 2.25 | 2 |
| 9A | RET | 0.25 | 38 | 2.5 | 2 |
| 9B | RET | 0.125 | 38 | 2.5 | 2 |
| 10A | RET | 0.25 | 40 | 2.5 | 2.5 |
| 10B | RET | 0.125 | 40 | 2.5 | 2 |
| 11A | RET | 0.25 | 43 | 3 | 2.5 |
| 11B | RET | 0.125 | 43 | 3 | 2.5 |
| 12A | RET | 0.25 | 45 | 2.5 | 2.5 |
| 12B | RET | 0.125 | 45 | 3 | 2.25 |
| 13A | RET | 0.25 | 48 | 3 | 3 |
| 13B | RET | 0.125 | 48 | 3 | 3 |
| 14A | RET | 0.25 | 50 | 3 | 2.5 |
| 14B | RET | 0.125 | 50 | 3 | 2.5 |

Using the hybridization buffer of the present disclosure result, the data in Table 23 underline that hybridization temperatures in a broad range from 38° C. to 50° C. results in acceptable signal intensities with the HER2/CEN-17 and RET BA probe sets at low concentration.

Example 7

Certain existing hybridization buffers often exhibit high viscosity which presents challenges with respect to handling, pipetting, and spreading in capillary fields. However, the hybridization buffers of the present disclosure exhibit lower viscosity while still supporting high quality FISH staining results. In this experiment, the viscosity of a hybridization buffer of the present disclosure is compared to the viscosity of a comparative control hybridization buffer at relevant temperatures of handling, such as 15, 20, 25, 32 and 37° C.

The hybridization buffer of the present disclosure (test) that was tested contained 13% (v/v) sulfolane, 10% (w/v) dextran sulfate, 30% (w/v) polyvinyl sulfonic acid sodium salt, 200 mM NaCl and 50 mM phosphate buffer, pH 7.4. The comparative control hybridization buffer contained 15% (v/v) ethylene carbonate, 20% (w/v) dextran sulfate, 600 mM NaCl and 10 mM Citrate buffer pH 6.2.

A microviscometer operating by the rolling ball principle was calibrated at 25° C. and used in accordance with manufacturer's instructions. Test hybridization buffer of the present disclosure or comparative control hybridization buffer were loaded to the system and recordings of viscosity and density at different temperatures were performed. Results from the viscosity and density measurements are presented in the following table (Table 24):

TABLE 24

| Hybridization buffer | Viscosity (mPa.s) | | | | |
|---|---|---|---|---|---|
| | 15° C. | 20° C. | 25° C. | 32° C. | 37° C. |
| Hybridization buffer of present disclosure | 51.57 | 44.28 | 38.11 | 31.98 | 28.33 |
| | 51.52 | 44.19 | 38.31 | 31.95 | 28.32 |
| | | | 38.40 | | |
| | | | 38.37 | | |
| Comparative control | 79.70 | 70.58 | 62.91 | 53.88 | 48.38 |

Figure 2:
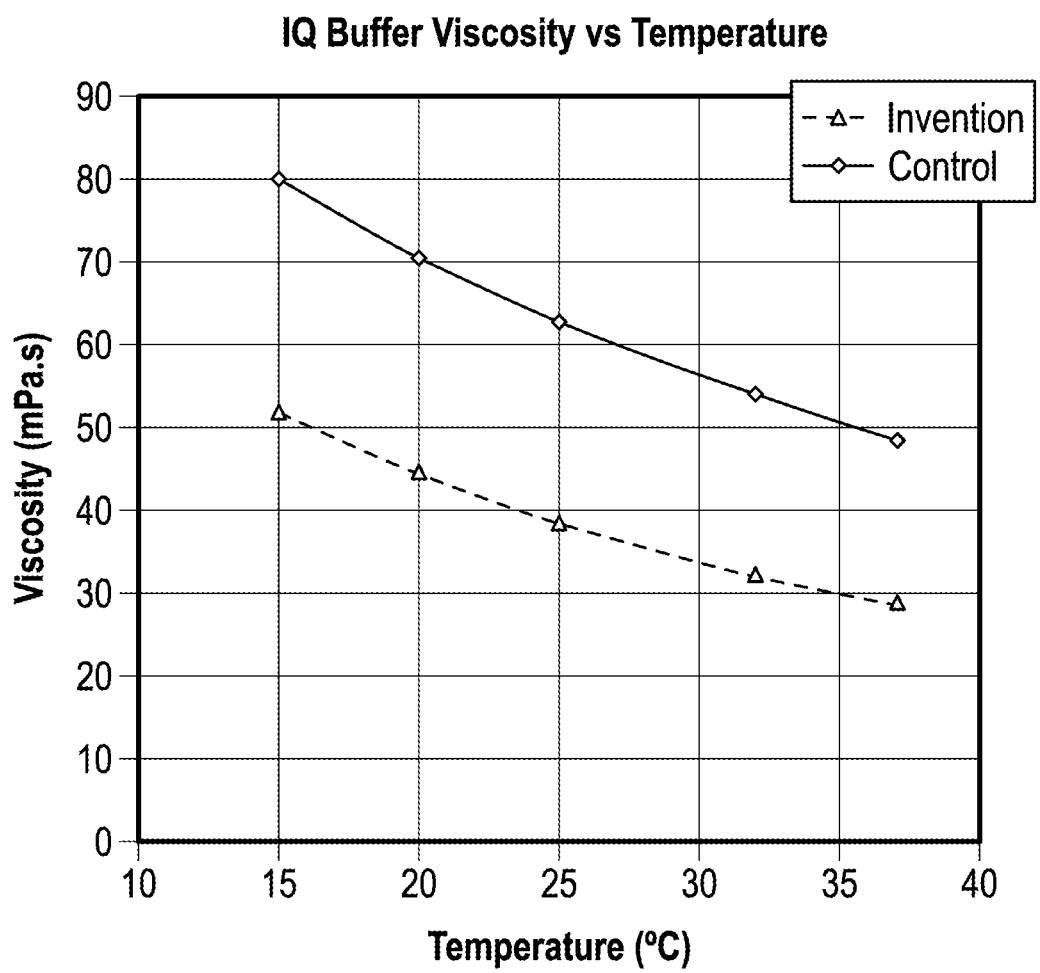
FIG. 2 provides a graphical representation demonstrating that the FISH hybridization buffers of the present disclosure are less viscous than certain existing FISH buffers.

Data from this experiment is summarized in FIG. 2 where viscosity is plotted on the y-axis versus temperature on the x-axis. This data demonstrates that the hybridization buffers of the present disclosure provide a reduction in viscosity from 62.9 mPa·s for the comparative control buffer to 38.3 mPa·s at 25° C. This corresponds to a decrease in viscosity of approximately 40%. At higher temperatures, the decrease is slightly above 40% and at lower temperatures the decrease is slightly less than 40% (see table above). These results confirm that the buffers of the present disclosure exhibit lower viscosities when compared to the comparative control hybridization buffers.

EXEMPLARY EMBODIMENTS

Exemplary embodiments provided in accordance with the presently disclosed subject matter include, but are not limited to, the following:

1. A hybridization buffer comprising a sulfone solvent in a concentration from about 5 to about 30% (v/v); and a sulfonic acid polymer of formula (I), (Ia), (II), (IIa) or (III):

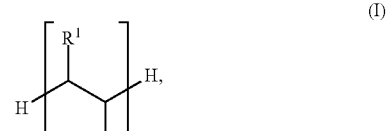

(I)

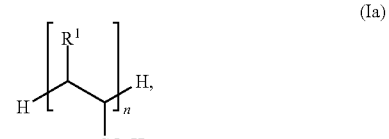

(Ia)

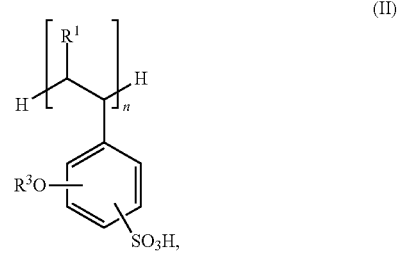

(II)

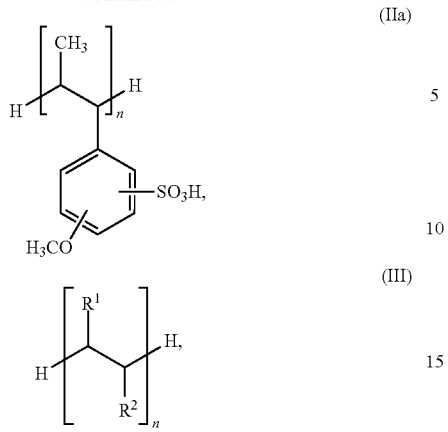

or a salt of any one of Formulas (I), (Ia), (II), (IIa) or (III), wherein: $R^1$ is hydrogen or $C_{1-6}$ aliphatic; L, when present, is a covalent bond or $C_{1-6}$ aliphatic, $R^2$, when present, is a covalent bond, $C_{1-6}$ aliphatic, phenyl, or a 6-membered heteroaryl ring having 1-3 nitrogens, wherein: $R^2$ is substituted with 1 or 2-$SO_3H$ groups or a salt thereof, provided that when $R^2$ is a covalent bond, only 1-$SO_3H$ or a salt thereof is present, and $R^2$ is optionally substituted with 1-2 groups independently selected from —$R^3$, halogen, —CN, —$NO_2$, —$OR^3$, —$N(R^3)_2$, and —$SR^3$, wherein each $R^3$ is independently hydrogen or a $C_{1-6}$ alkyl group; and n is an integer greater than 10; and wherein the sulfonic acid polymer or salt thereof is present in a concentration from about 5 to about 50% (w/v).

2. The hybridization buffer of embodiment 1, wherein $R^1$ is hydrogen.
3. The hybridization buffer of embodiment 1 wherein $R^1$ is $C_{1-6}$ aliphatic.
4. The hybridization buffer of any one of embodiments 1-3 wherein L is a covalent bond.
5. The hybridization buffer of any one of embodiments 1-3 wherein L is $C_{1-6}$ aliphatic.
6. The hybridization buffer of any one of embodiments 1-3 wherein L is methylene.
7. The hybridization buffer of any one of embodiments 1-6, further comprising water.
8. The hybridization buffer of any one of embodiments 1-7, wherein the sulfonic acid polymer or salt thereof is polyvinylsulfonic acid or a salt thereof.
9. The hybridization buffer of any one of embodiments 1-8, wherein the concentration of the sulfone solvent is from about 10% to about 20% (v/v).
10. The hybridization buffer of any one of embodiments 1-9, wherein the sulfone solvent is selected from the group consisting of dimethyl sulfone, diphenyl sulfone, methyl phenyl sulfone, tetramethylene sulfone (sulfolane), and mixtures thereof.
11. The hybridization buffer of any one of embodiments 1-10, wherein the sulfone solvent is sulfolane.
12. The hybridization buffer of any one of embodiments 1-11, wherein the concentration of the sulfonic acid polymer or salt thereof is from about 20% to about 40% (w/v).
13. The hybridization buffer of any one of embodiments 1-12, further comprising dextran sulfate in concentration no greater than 20% (w/v), alternatively no greater than 15% (w/v), alternatively no greater than 10% (w/v).
14. The hybridization buffer of any one of embodiments 1-13, wherein the hybridization buffer has a viscosity at 25° C. of about 60 mPa·s or less, alternatively about 50 mPa·s or less, alternatively about 40 mPa·s or less, as measured by microviscometry.
15. The hybridization buffer of any one of embodiments 1-14, wherein the hybridization buffer is stable at 2-8° C. for at least 2 months, alternatively for at least 4, 6, 8, 12, 16, 18 or 24 months.
16. The hybridization buffer of any one of embodiments 1-15, wherein the hybridization buffer is homogeneous after storage at 2-8° C. for at least 2 months, alternatively for at least 4, 6, 8, 12, 16, 18 or 24 months.
17. The hybridization buffer of any of embodiments 1-16, wherein the hybridization buffer maintains homogeneity after storage at 2-8° C. for at least 2 months, alternatively for at least 4, 6, 8, 12, 16, 18 or 24 months, wherein the homogeneity is determined by visually assessing the clarity of the hybridization buffer following centrifugation of the hybridization buffer with erioglaucine.
18. The hybridization buffer of any one of embodiments 1-17, further comprising at least one additional component selected from the group consisting of buffering agents, salts, accelerating agents, chelating agents, detergents, blocking agents, and combinations thereof.
19. The hybridization buffer of any one of embodiments 1-18, further comprising NaCl and 3-(N-morpholino) propanesulfonic acid (MOPS).
20. The hybridization buffer of any one of embodiments 1-19, further comprising an accelerating agent in a concentration no greater than about 20% (w/v), alternatively no greater than about 10% (w/v), a salt, and a buffering agent; wherein the sulfone solvent is sulfolane in a concentration of about 10% (v/v), the sulfonic acid polymer or salt thereof is in a concentration of about 30% (w/v).
21. A hybridization composition comprising the hybridization buffer of any of embodiments 1-20, and at least one nucleic acid probe.
22. A method of hybridizing nucleic acid sequences comprising applying at least one nucleic acid probe and a hybridization buffer to the target nucleic acid sequence for at least a time period sufficient to hybridize the at least one nucleic acid probe to the target nucleic acid sequence, wherein the hybridization buffer comprises a sulfone solvent in a concentration from about 5 to about 30% (v/v) and a sulfonic acid polymer of formula (I), (Ia), (II), (IIa) or (III):

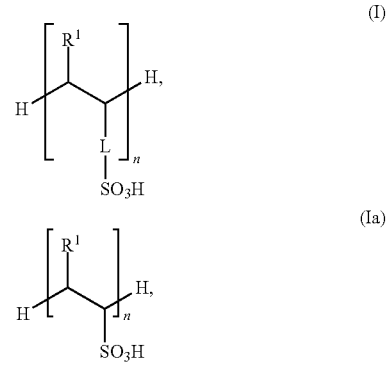

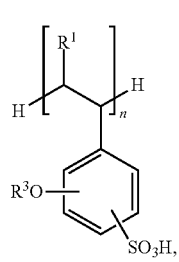

(II)

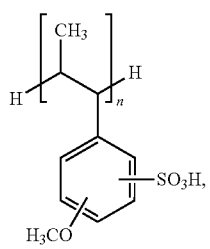

(IIa)

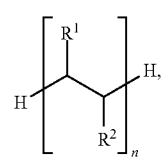

(III)

or a salt of any one of Formulas (I), (Ia), (II), (IIa) or (III), wherein: $R^1$ is hydrogen or $C_{1-6}$ aliphatic; L, when present, is a covalent bond or $C_{1-6}$ aliphatic, $R^2$, when present, is a covalent bond, $C_{1-6}$ aliphatic, phenyl, or a 6-membered heteroaryl ring having 1-3 nitrogens, wherein: $R^2$ is substituted with 1 or 2-$SO_3H$ groups or a salt thereof, provided that when $R^2$ is a covalent bond, only 1-$SO_3H$ group or a salt thereof is present, and $R^2$ is optionally substituted with 1-2 groups independently selected from —$R^3$, halogen, —CN, —$NO_2$, —$OR^3$, —$N(R^3)_2$, and —$SR^3$, wherein each $R^3$ is independently hydrogen or a $C_{1-6}$ alkyl group; and n is an integer greater than 10; and wherein the sulfonic acid polymer or salt thereof is present in a concentration from about 5 to about 50% (w/v).

23. The method of embodiment 22, wherein the target nucleic acid sequence is present in an in situ biological sample.
24. The method of any of embodiments 22-23, further comprising denaturing the target nucleic acid sequence at a temperature of about 65° C. or higher.
25. The method of any of embodiments 22-24, wherein the time period sufficient to hybridize the at least one nucleic acid probe to the target nucleic acid sequence is four hours or less.
26. The method of any of embodiments 22-25, wherein hybridization of the at least one nucleic acid probe to the target nucleic acid is conducted at a temperature of 50° C. or lower.
27. The method of any of embodiments 22-26, further comprising obtaining the hybridization buffer from storage at a temperature of 8° C. or lower; combining the hybridization buffer with the at least one nucleic acid probe without mixing the hybridization buffer prior to combining the probe therewith.
28. The method of any of embodiments 22-27, wherein the sulfone solvent is selected from the group consisting of dimethyl sulfone, diphenyl sulfone, methyl phenyl sulfone, tetramethylene sulfone (sulfolane), and mixtures thereof.
29. The method of any of embodiments 22-28, wherein the sulfone solvent is sulfolane.
30. A method of preparing a hybridization composition comprising storing a hybridization buffer at a temperature for at least 2 months, alternatively for at least 4, 6, 8, 12, 16, 18 or 24 months; and subsequently combining the hybridization buffer with at least one nucleic acid probe to form a hybridization composition.
31. The method of embodiment 30, wherein the hybridization buffer is stored at a temperature greater than 0° C.

The foregoing description of exemplary or preferred embodiments should be taken as illustrating, rather than as limiting the present invention as defined by the embodiments. As will be readily appreciated, numerous variations and combinations of the features set forth above can be utilized without departing from the present invention as set forth in the embodiments. Such variations are not regarded as a departure from the scope of the invention, and all such variations are intended to be included within the scope of the following embodiments. All references cited herein are incorporated by reference in their entireties.

I claim:
1. An in situ hybridization buffer comprising:
a sulfone solvent in a concentration from 5 to 30% (v/v); and
a sulfonic acid polymer of formula (I), (Ia), (II), (IIa) or (III):

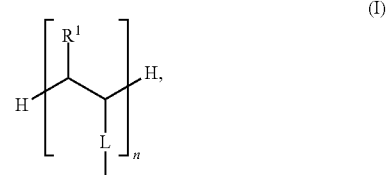

(I)

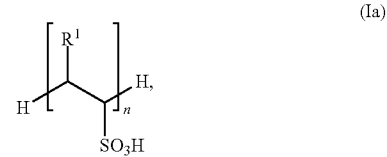

(Ia)

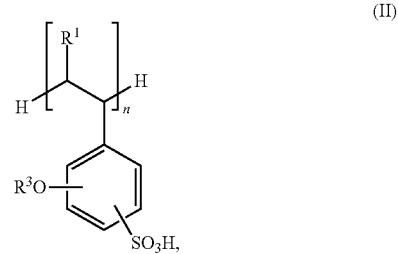

(II)

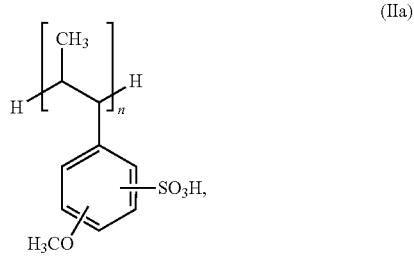

(IIa)

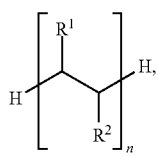

or a salt of any one of Formulas (I), (Ia), (II), (IIa) or (III), wherein: $R^1$ is hydrogen or $C_{1-6}$ aliphatic; L, when present, is a covalent bond or $C_{1-6}$ aliphatic, $R^2$, when present, is a covalent bond, $C_{1-6}$ aliphatic, phenyl, or a 6-membered heteroaryl ring having 1-3 nitrogens, wherein: $R^2$ is substituted with 1 or 2-$SO_3H$ groups or a salt thereof, provided that when $R^2$ is a covalent bond, only 1-$SO_3H$ group or a salt thereof is present, and $R^2$ is optionally substituted with 1-2 groups independently selected from —-$R^3$, halogen, —CN, —$NO_2$, —$OR^3$, —$N(R^3)_2$, and —$SR^3$, wherein each $R^3$ is independently hydrogen or a $C_{1-6}$ alkyl group; and n is an integer greater than 10; and wherein the sulfonic acid polymer or salt thereof is present in a concentration from 5 to 50% (w/v); and wherein the hybridization buffer is homogeneous without phase separation after storage at 2-8° C. for 2-24 months.

2. The hybridization buffer of claim 1, wherein $R^1$ is hydrogen.

3. The hybridization buffer of claim 1, wherein $R^1$ is $C_{1-6}$ aliphatic.

4. The hybridization buffer of claim 1, wherein L is a covalent bond.

5. The hybridization buffer of claim 1, wherein L is $C_{1-6}$ aliphatic.

6. The hybridization buffer of claim 1, wherein L is methylene.

7. The hybridization buffer of claim 1, further comprising water.

8. The hybridization buffer of claim 1, wherein the sulfonic acid polymer or salt thereof is polyvinylsulfonic acid or a salt thereof.

9. The hybridization buffer of claim 1, wherein the concentration of the sulfone solvent is from 10% to 20% (v/v).

10. The hybridization buffer of claim 1, wherein the sulfone solvent is selected from the group consisting of dimethyl sulfone, diphenyl sulfone, methyl phenyl sulfone, tetramethylene sulfone (sulfolane), and mixtures thereof.

11. The hybridization buffer of claim 1, wherein the sulfone solvent is sulfolane.

12. The hybridization buffer of claim 1, wherein the concentration of the sulfonic acid polymer or salt thereof is from 20% to 40% (w/v).

13. The hybridization buffer of claim 1, further comprising dextran sulfate in concentration no greater than 20% (w/v).

14. The hybridization buffer of claim 1, wherein the hybridization buffer has a viscosity at 25° C. of 60 mPa·s, as measured by microviscometry.

15. The hybridization buffer of claim 1, wherein the hybridization buffer is stable at 2-8° C. for 2-24 months.

16. The hybridization buffer of claim 1, further comprising NaCl and 3-(N-morpholino) propanesulfonic acid (MOPS).

17. The hybridization buffer claim 1, further comprising:
an accelerating agent in a concentration no greater than 20% (w/v), wherein
the sulfone solvent is sulfolane in a concentration of 10% (v/v),
the sulfonic acid polymer or salt thereof is in a concentration of 30% (w/v).

* * * * *